(12) United States Patent
Drugmand et al.

(10) Patent No.: US 10,280,391 B2
(45) Date of Patent: May 7, 2019

(54) RECIPIENT FOR CELL CULTIVATION

(71) Applicants: PALL TECHNOLOGY UK LIMITED, Portsmouth (GB); PALL LIFE SCIENCES BELGIUM, Hoegaarden (BE); PALL ARTELIS BVBA, Brussels (BE)

(72) Inventors: Jean-Christophe Drugmand, Louvain-la-Neuve (BE); Jose Antonio Castillo Gonzalez, Brussels (BE); Vishwas Pethe, Shakopee, MN (US); Matthew Kremer, Philadelphia, PA (US)

(73) Assignee: PALL TECHNOLOGY UK LIMITED, Portsmouth (GB)

( * ) Notice: Subject to any disclaimer, the term of this patent is extended or adjusted under 35 U.S.C. 154(b) by 164 days.

(21) Appl. No.: 14/648,590

(22) PCT Filed: Dec. 11, 2013

(86) PCT No.: PCT/US2013/074307
§ 371 (c)(1),
(2) Date: May 29, 2015

(87) PCT Pub. No.: WO2014/093444
PCT Pub. Date: Jun. 19, 2014

(65) Prior Publication Data
US 2015/0299634 A1 Oct. 22, 2015

Related U.S. Application Data

(60) Provisional application No. 61/735,841, filed on Dec. 11, 2012.

(51) Int. Cl.
*C12M 1/00* (2006.01)
*C12M 1/26* (2006.01)
(Continued)

(52) U.S. Cl.
CPC ............ *C12M 23/34* (2013.01); *C12M 23/26* (2013.01); *C12M 25/14* (2013.01); *C12M 25/18* (2013.01);
(Continued)

(58) Field of Classification Search
CPC ...... C12M 23/26; C12M 23/34; C12M 25/14; C12M 25/18; C12M 27/12; C12M 29/14;
(Continued)

(56) References Cited

U.S. PATENT DOCUMENTS 4,322,296 A 3/1982 Fan
4,720,462 A 1/1988 Rosenson
(Continued)

FOREIGN PATENT DOCUMENTS

CN 1750868 A 3/2006
CN 1878858 A 12/2006
(Continued)

*Primary Examiner* — Michael L Hobbs
(74) *Attorney, Agent, or Firm* — King & Schickli, PLLC

(57) ABSTRACT

A recipient for cell cultivation having an inner compartment adapted for cell growth, in one embodiment, an outer tubular wall extends in a longitudinal direction and delimits an outer boundary of the inner compartment in a radial direction. First and second ends delimit the inner compartment at the first respectively the second outer end of the outer tubular wall. A fixed packing in the inner compartment comprises a packing, such as a fiber matrix. Additional embodiments and related methods are also disclosed.

15 Claims, 14 Drawing Sheets

(51) Int. Cl.
*C12M 1/12* (2006.01)
*C12M 3/04* (2006.01)

(52) U.S. Cl.
CPC ............ *C12M 27/12* (2013.01); *C12M 29/14* (2013.01); *C12M 33/08* (2013.01); *C12M 33/12* (2013.01); *C12M 33/14* (2013.01); *C12M 33/18* (2013.01); *C12M 47/02* (2013.01)

(58) Field of Classification Search
CPC ...... C12M 33/08; C12M 33/12; C12M 33/14; C12M 33/18; C12M 47/02
See application file for complete search history.

(56) References Cited

U.S. PATENT DOCUMENTS

| | | | |
|---|---|---|---|
| 5,266,476 A | 11/1993 | Sussman et al. | |
| 5,376,548 A * | 12/1994 | Matsuo | C12M 25/18 435/297.2 |
| 5,432,087 A | 7/1995 | Spielmann | |
| 5,527,705 A | 6/1996 | Mussi | |
| 5,728,577 A | 3/1998 | Kuriyama | |
| 5,958,761 A | 9/1999 | Yogev | |
| 6,150,159 A * | 11/2000 | Fry | C12M 23/08 435/298.2 |
| 6,720,178 B1 * | 4/2004 | Berson | C12M 23/34 366/235 |
| 8,137,959 B2 | 3/2012 | Castillo Fernandez | |
| 2002/0155594 A1 | 10/2002 | Hsieh et al. | |
| 2003/0175853 A1 | 9/2003 | Clarke et al. | |
| 2004/0058436 A1 | 3/2004 | Zhang et al. | |
| 2004/0110273 A1 | 6/2004 | Akers et al. | |
| 2011/0281343 A1 | 11/2011 | Gay | |
| 2012/0248111 A1 * | 10/2012 | Bear | B01L 3/50825 220/212 |

FOREIGN PATENT DOCUMENTS

| | | |
|---|---|---|
| CN | 1942575 A | 4/2007 |
| CN | 101087873 A | 12/2007 |
| DE | 102008039812 A1 | 3/2010 |
| EP | 0700990 A2 | 3/1996 |
| EP | 1245670 A2 | 10/2002 |
| EP | 1260580 A1 | 11/2002 |
| JP | 04063584 | 2/1992 |
| JP | 08173145 | 9/1994 |
| JP | H-09-056372 A | 3/1997 |
| WO | 9209681 A1 | 6/1992 |
| WO | 9519424 A1 | 7/1995 |
| WO | 2009139703 A1 | 11/2009 |
| WO | 2011133437 A2 | 10/2011 |
| WO | 2012140519 A2 | 10/2012 |

* cited by examiner

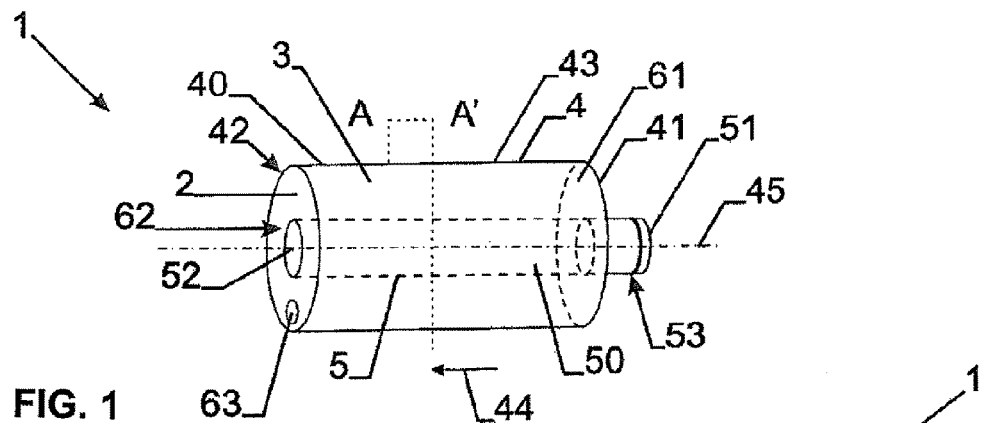
FIG. 1
FIG. 1A
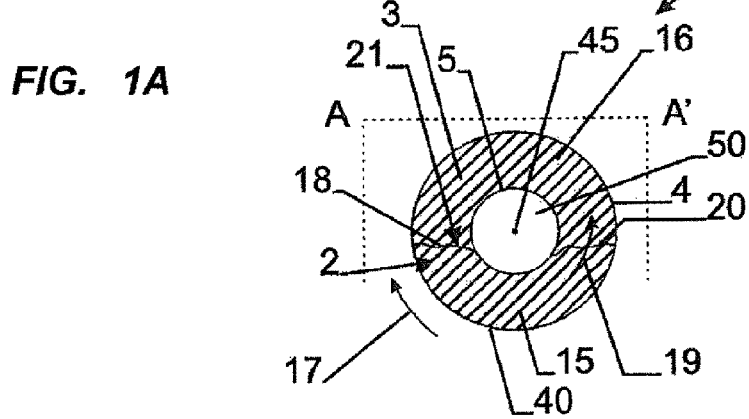
FIG. 2
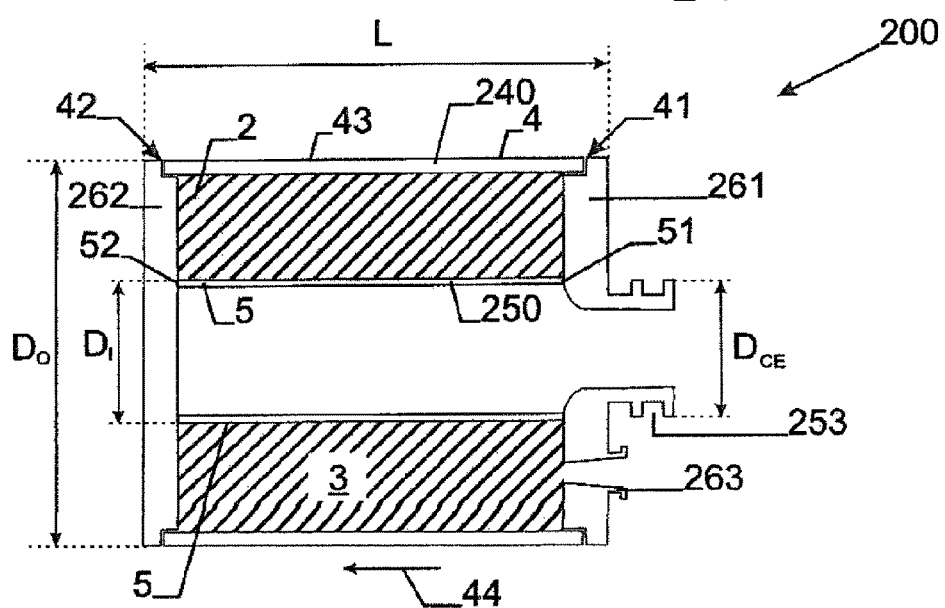

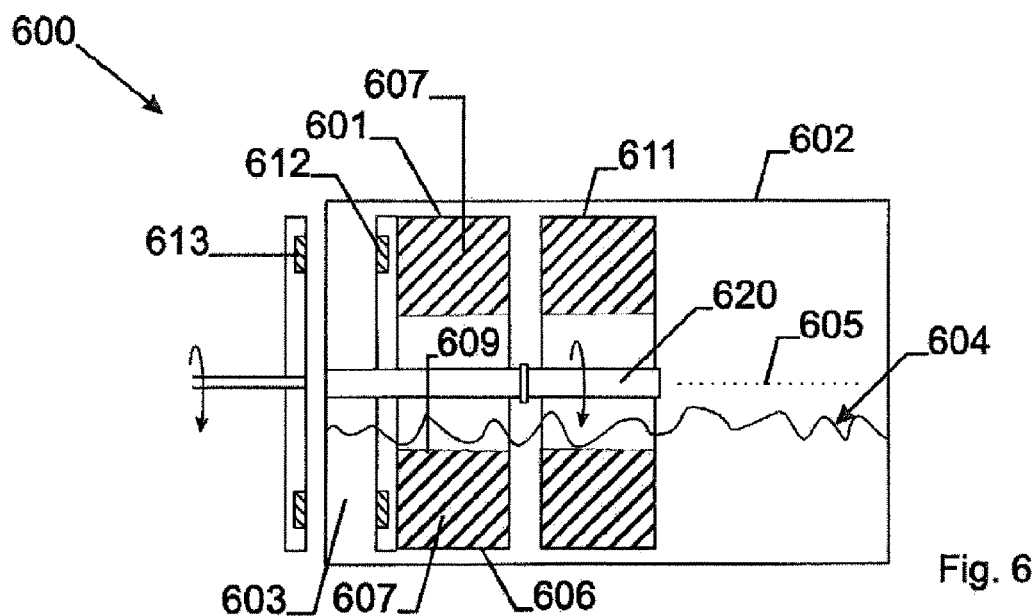
Fig. 6
FIG. 6A
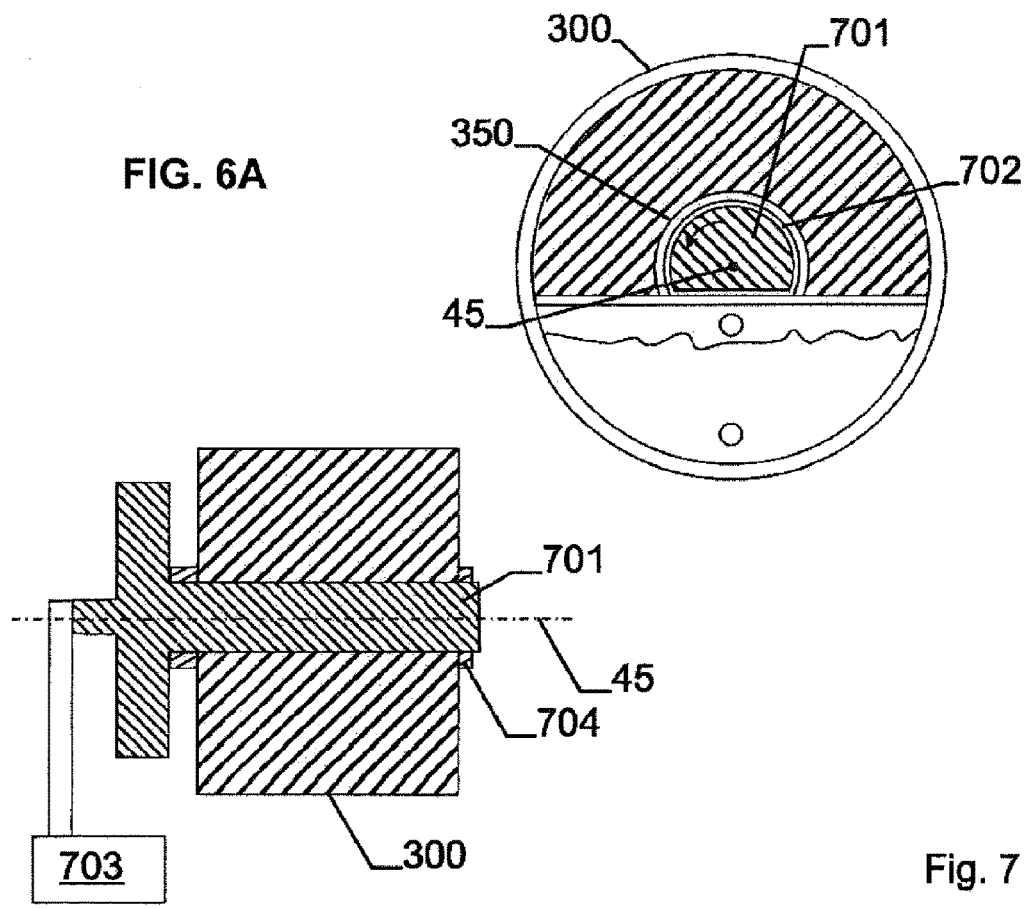
Fig. 7

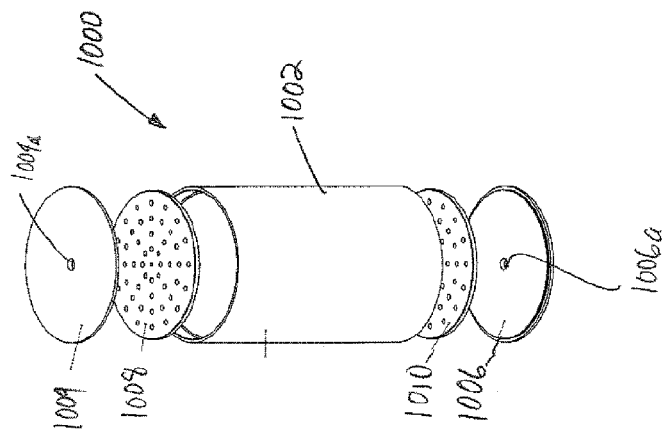
FIG. 10
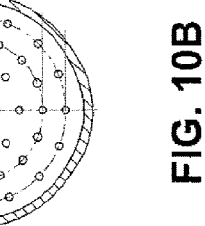
FIG. 10B
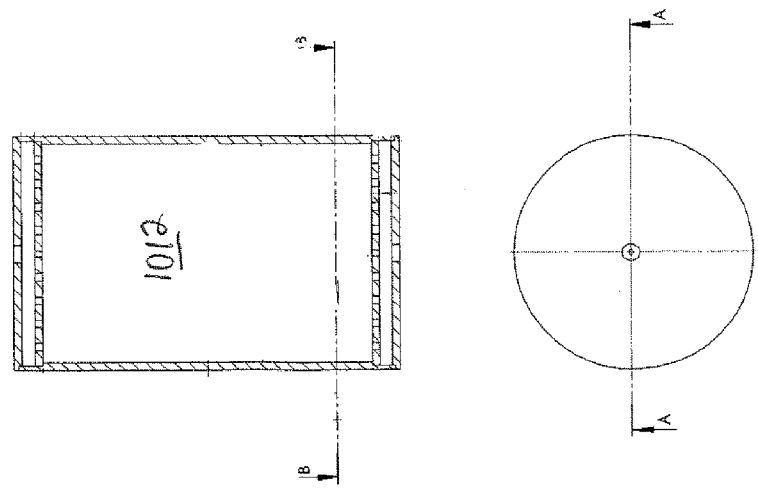
FIG. 10A
FIG. 10C

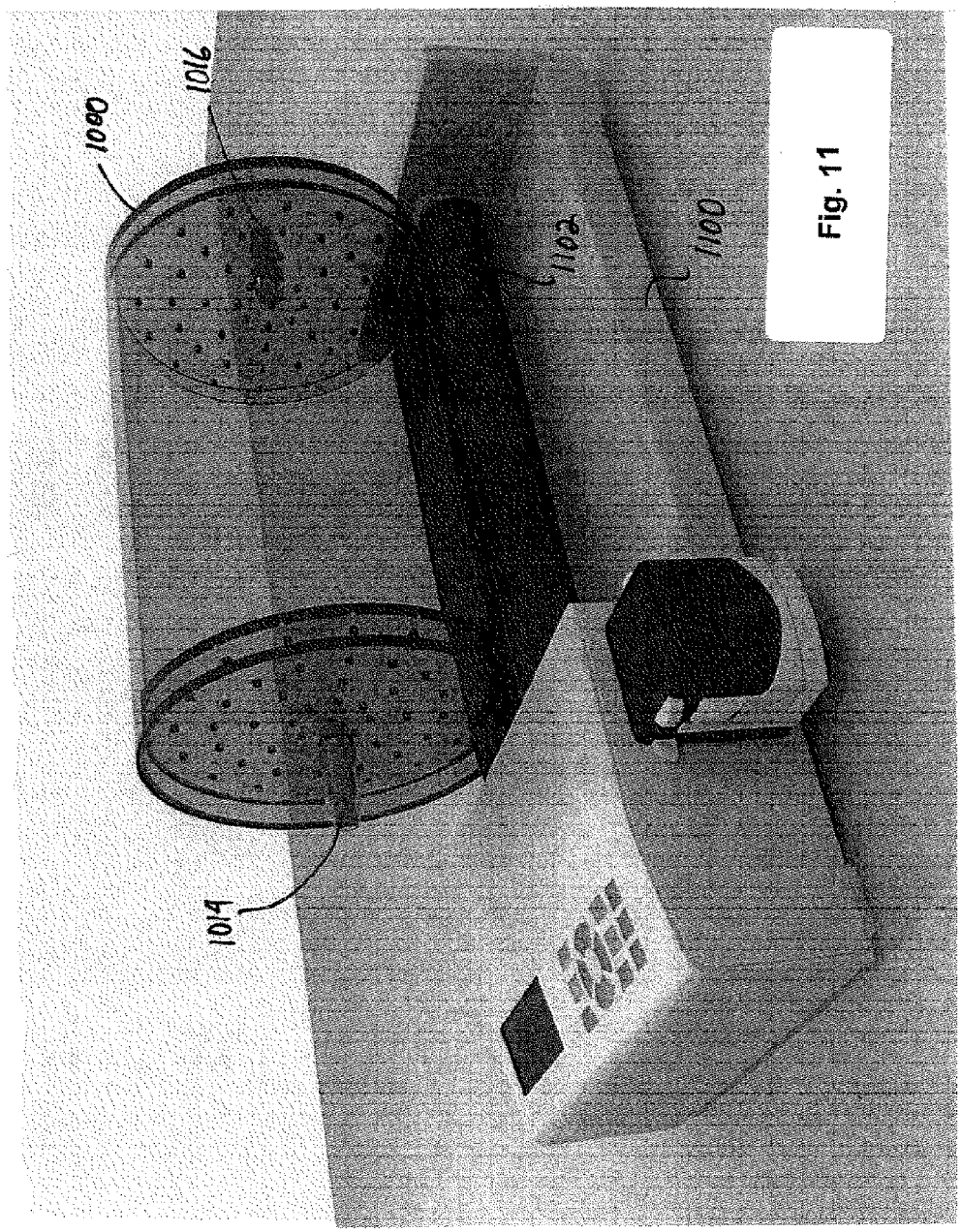

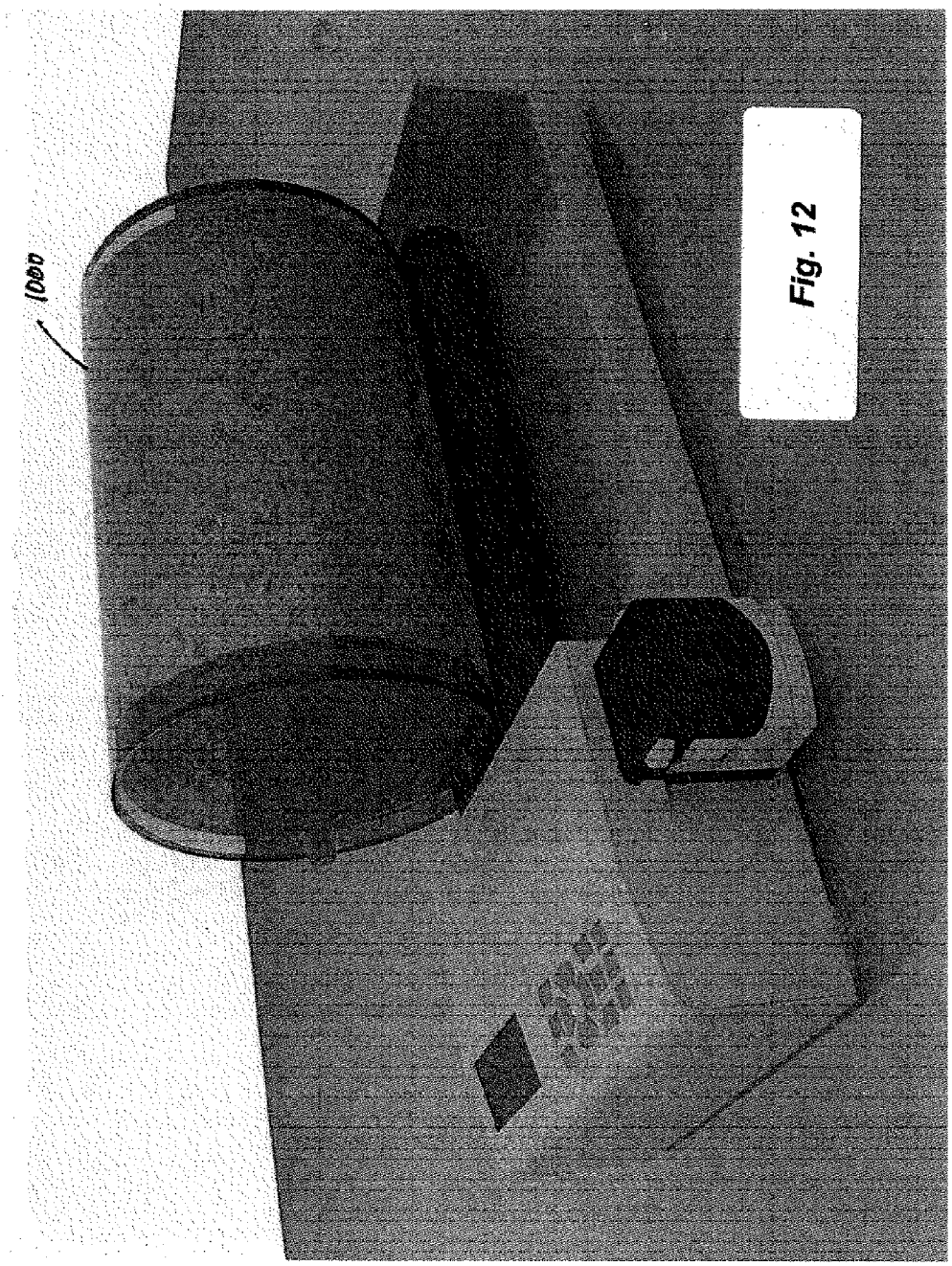

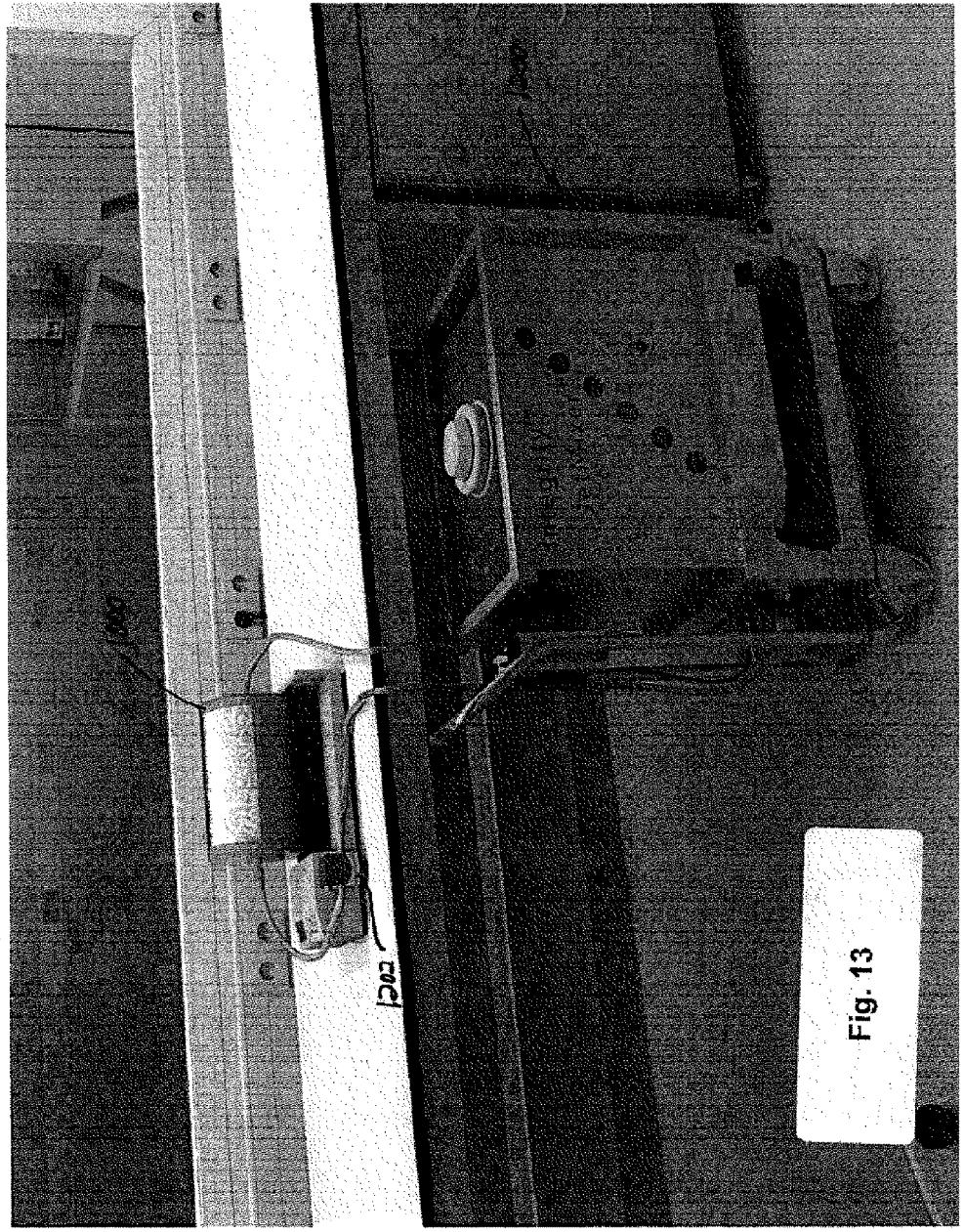

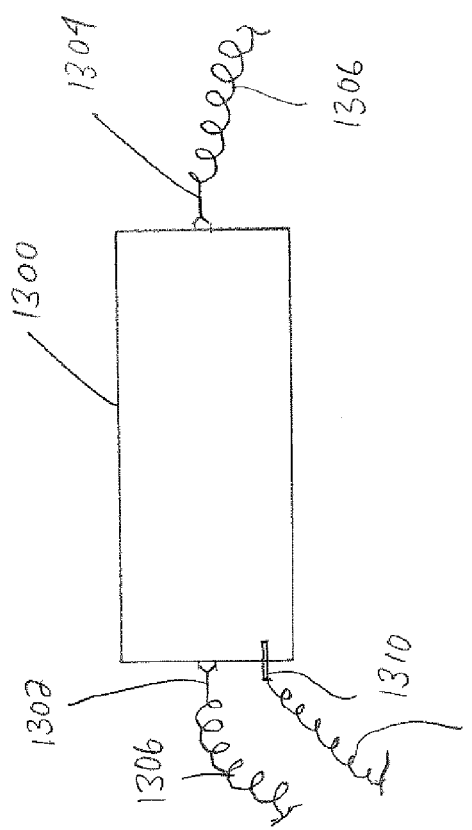
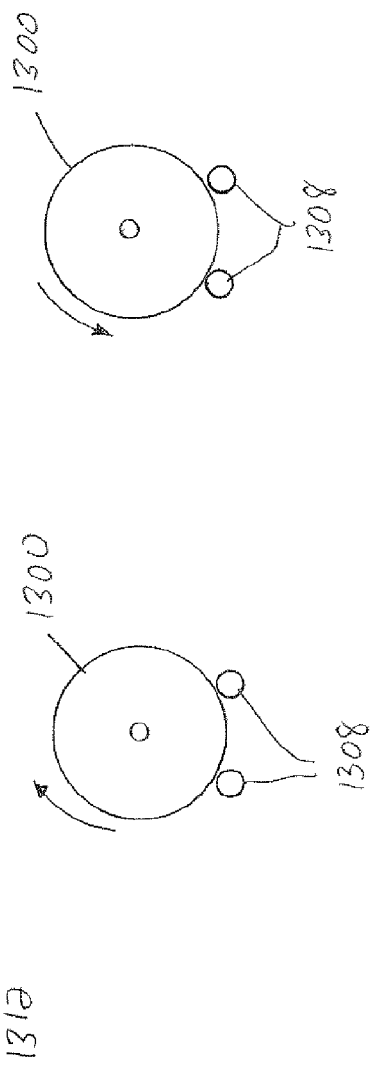
Fig. 14
Fig. 15
Fig. 16

US 10,280,391 B2

RECIPIENT FOR CELL CULTIVATION

This application is the U.S National Phase Application under 35 U.S.C. § 371 of International Application No. PCT/US2013/074307 filed Dec. 11, 2013 which claims the benefit of U.S. Provisional Patent Application Ser. No. 61/735,841 filed on Dec. 11, 2012, the disclosures of which are incorporated herein by reference.

TECHNICAL FIELD

This disclosure relates to recipient for cell cultivation, bioreactors comprising recipients for cell cultivation, methods of making such recipients or bioreactors and a method for using the recipient or bioreactor, e.g. the cultivating cells.

BACKGROUND

In cell cultivation nowadays, the yield of a bioreactor comprising one or more recipients is one of the main concerns of the bio-industry. The complexity of current approaches can also increase costs. Accordingly, a need for improvement is identified.

SUMMARY

It is an object of embodiments disclosed herein to provide good recipients and methods for cell cultivation. An advantage can be that the recipients, when used for cell growth, may have a yield at least equal to or even larger than the yield of presently known recipients, and without increased complexity or cost. It is an advantage to provide recipients which have an increased cell density providing an increased "volumetric yield", being the yield per volume of the recipient. It is an advantage to provide recipients, when used for cell growth that may have substantially uniform cell cultivation throughout the recipient. It is an advantage to provide recipients, when used for cell growth, have a more uniform aeration and refreshment of the medium along the whole surface upon which cells are to grow. It is an advantage to provide recipients providing good cell growth and/or improved viability maintenance. It is an advantage to provide recipients that can be used to manufacture disposable recipients and bioreactors.

A method and a recipient may accomplish one or more of the above objectives.

According to a first aspect, the embodiments of a recipient for cell cultivation according to the disclosure have an inner space containing packing compatible with cell growth. The inner space is defined by:
  an outer tubular wall having a first and a second outer end,
  an inner elongate wall having a first outer end oriented towards the first outer end of the outer tubular wall, and a second outer end oriented towards the second outer end of the outer tubular wall, the inner elongate wall being positioned within the outer tubular wall, and
  a first and a second closure for closing the inner space.

The recipient for cell cultivation may have an annular inner space containing packing compatible with cell growth. When present, this annular inner space has an annular volume being delimited by:
  an outer tubular wall having a first and a second outer end and a longitudinal wall extending in longitudinal direction, the outer tubular wall delimiting an outer boundary of the annular volume in longitudinal direction;
  a first and a second closure delimiting and closing the annular volume at the first respectively the second outer end of the outer tubular wall;
  an inner elongate wall having a first outer end oriented towards the first outer end of the outer tubular wall, and a second outer end oriented towards the second outer end of the outer tubular wall, the inner elongate wall being positioned within the outer tubular wall, the inner elongate wall extending in longitudinal direction and delimiting an inner boundary of the annular volume, the inner boundary being encompassed by the outer boundary.

Optionally the inner boundary is enclosed by the outer boundary.

The first outer end of the inner elongate wall may coincide with the first closure. The second outer end of the inner elongate wall may coincide with the second closure.

The inner elongate wall may be provided by an inner elongate element. The outer tubular wall may be provided by an outer tubular element.

It is an advantage that substantially the complete volume of cultivation medium, such as cell cultivation medium, provided in the recipient for enabling cell cultivation, may be forced to flow through the packing.

According one embodiment, the smallest cylinder circumscribing the outer boundary, and having its axis in longitudinal direction, may have a diameter Dmax; the distance between inner boundary and outer boundary in radial direction may be in a range between 5% and 45% of Dmax.

The annular inner space having an annular volume has the advantage that during cell growth, upon rotating the recipient which is at least partially filled with cultivation medium, such as cell cultivation medium, the medium may flow through the packing according to a substantially uniform and/or constant flow rate. The medium may even flow through the packing according to a plug flow. A more uniform and predictable cell growth may be obtained. Optionally a higher yield is obtained. In case medium and gas, e.g. oxygen or carbon dioxide, is to be mixed for allowing cells to grow, the predictable and more uniform flow of medium through the packing may result in a more uniform aeration of the packing, and hence may increase the efficiency of cell growth throughout the packing. This is in particular the case when the cultivation medium, such as cell cultivation medium, flows through the packing as a plug flow.

Upon penetrating of the cultivation medium, such as cell cultivation medium into a given region of the packing, the present gas or air is forced to displace, e.g. flow out of this region. Once the volume of cultivation medium, such as cell cultivation medium has passed the region, a depression is created behind the volume of the displaced cultivation medium, such as cell cultivation medium. This depression causes gas or air present in an adjacent packing region, to be sucked to the region where the depression is present. As such, not only the cultivation medium, such as cell cultivation medium is displaced through the packing, but also the gas or air present in the recipient.

The cultivation medium, such as cell cultivation medium, in particular the composition of the medium, may be adapted to the yield obtained. In particular embodiments the medium is enriched with spore elements or additional carbon sources for e.g. transient or constitutive expression. In other particular embodiments a minimal medium is used, for example for labelling experiments (e.g. NMR labelling).

The recipient according to the first aspect may be part of a bioreactor for cell cultivation. The recipient may be rotatably mounted in the bioreactor, whereby the recipient is rotated around an axis substantially parallel to the longitudinal direction of the recipient, i.e. the longitudinal direction of the outer tubular wall. The closures close the annular volume at the two outer ends of the outer tubular wall. This prevents medium present in the volume to leak from the annular volume in lateral direction at the height of these closures.

In any embodiment, the packing may be a packing suitable for adherent cell growth. The packing may be a packing suitable for suspension culture. The packing may be selected from the group consisting of woven or non-woven microfibers, porous carbon and matrices of chitosans. The microfibers may optionally be made of PET or any other polymer or biopolymer. The polymers may be treated to be compatible with cell culture, if such treatment is necessary.

Suitable packing or "carrying material" are mineral carriers such as silicates, calcium phosphate, organic compounds such porous carbon, natural products such as chitosan, polymers or biopolymers composititible with cells growth. The packing can have the form of beads with regular or irregular structure, or may comprising woven or non-woven microfibers of a polymer or any other material compatible with cell growth. The packing can also be provided as a single piece with pores and or channels. The packing in the recipients can have a variety of forms and dimensions. In some embodiments the packing is a particulate material of solid or porous spheres, flakes, polygons. Typically a sufficient amount of packing is used to avoid movement of the packing particles within the recipient upon use, as this may damage cells and may have an influence on the circulation of gas and/or medium. Alternatively the packing consists of an element which fits into the inner recipient or into a compartment of the recipient, and having an adequate porosity and surface. The porosity of packing in accordance with certain embodiments ranges from 60% to 99%, more particularly from 80% to 90%. For adherent cell growth the accessible surface to cells for the packing is between about 150 and 1000 $cm^2$ per $cm^3$. An example hereof is a carbon matrix (Carboscale) manufactured by Cinvention (Germany).

The outer tubular wall, the inner elongate element, the closures and optionally other elements of the recipient may be provided of material suitable for recipients for cell cultivation, such as stainless steel, polystyrene, glass, polyethylene, polysulfone, methyl methacrylate, high density polyethylene, low density polyethylene, polyethylene terephthalate glycol, perfluoroalkoxy, polycarbonate, polyvinylidene fluoride, polytetrafluoroethylene, ultra high molecular weight polyethylene, nylon, Teflon, crystalline polystyrene, metallocene-based polypropylenes, or syndiotatic polystyrene. In one embodiment, wherein the cells are grown in suspension, the elements of the recipient are treated, if necessary, with compounds to prevent cell adhesion. In another embodiment, wherein the cells are grown as adherent cells, the elements of the recipients are, if necessary, treated with compounds such as polylysine to obtain the desired adherence.

The recipient further may comprise at least a first and a second fluid permeable divider dividing the inner space in at least two compartments, wherein:
  the fluid permeable dividers extend from the inner elongate wall to the outer tubular wall and from the first closure to the second closure in a longitudinal direction parallel to the direction of the tubular axis, and
  one of said first and second compartments does not contain packing.

The recipient further may comprise at least N fluid permeable dividers, dividing the inner space in at least N compartments, N being an integer equal or larger than 2. The fluid permeable dividers may extend from the inner elongate wall to the outer tubular wall and from the first closure to the second closure in a longitudinal direction parallel to the direction of the tubular axis Optionally at most N−1 compartments are provided with said packing. Optionally, N is an even integer, and N/2 compartments are provided with said packing. In case N is equal or larger than 2, each compartment comprising said packing may adjoin two compartments without packing.

In case the outer tubular wall is a cylindrical wall, the inner space may be divided in a plurality of compartments extending in a direction parallel to the direction of the longitudinal direction of the outer tubular wall.

The compartment without packing may have a volume of between 25 to 90 percent of the annular volume of the inner space.

The fluid permeable dividers may be permeable for liquids and gas and may be suitable to retain the packing.

The dividers may be provided from porous material, which pores having a size suitable to render the divider permeable for liquids and gas, and small enough to enable the divider to retain the packing.

Alternatively the dividers may be impermeable for the liquids and gasses used. As such, the open space is divided in a plurality of sub-units, of which each sub-unit may be provided with suitable packing.

At least one of the first and second closures may be provided with at least one connector for providing and/or extracting medium and/or gas to and/or from the inner space.

The connector may comprise a snap fitting or tight fitting, or may be any other suitable connector. The connector or connectors may be connected to a flexible conduit or tubing or ducts, which guide medium to or from the inner space. In a particular embodiment, a tight fitting is connected to a flexible tubing.

The composition of the medium depends on the type of cells under consideration. These media are well known to the skilled person and are commercially available from various manufacturers. In view of the high cell densities which are obtained with the recipients of embodiments of the present invention, the medium is in particular embodiments enriched with carbon sources, spore elements, vitamins, amino acids and the like. In particular embodiments the medium is further supplied with surfactants to adapt the rheological properties of the medium. The gas is generally air for the growth of bacteria and yeast, while mammalian cells are typically grown in a mixture of 95% air and 5% $CO_2$. In particular embodiments of the methods of the present invention the gas in the recipients is monitored for oxygen and/or $CO_2$ depletion and either replaced or supplemented with oxygen or $CO_2$ At least one of the first and second closures may be provided with at least one connector for providing and/or extracting medium and/or gas to and/or from the inner space. The at least one closure may comprise the at least one connector being positioned such that the at least one connector is suitable for providing and/or extracting medium and/or gas to and/or from the compartment wherein no packing is present. At least one of the first and second closures may comprise more than one connector for providing and/or extracting medium and/or gas to and/or from the inner space.

In case the at least one of the first and second closures comprising the at least one connector and the outer tubular wall are disconnectable, the at least one connector is suitable to be positioned such that the at least one connector is for providing and/or extracting medium and/or gas to and/or from the compartment wherein no packing is present.

The at least one connector may comprise a tight fitting for connecting a flexible conduit.

The at least one connector may be positioned in the closure near the outer tubular wall.

The opening may be located in contact with the outer tubular wall.

The inner elongate element may be centrally positioned within the outer tubular wall.

The outer tubular wall may be provided by a cylindrical tubular element.

The inner elongate wall may be provided by a cylindrical element.

The inner elongate element may be coaxially positioned within the outer tubular wall.

The inner elongate element may have a radial cross-section according to a plane perpendicular to its longitudinal direction. The radial cross-section may have a shape selected from the group of a circle, oval, ellipse, square, rectangle and a circular segment.

The radial cross-section may have a circular segment shape, which segment has a central angle larger than 180°. This embodiment has the advantage that, when the recipient is rotated about an axis, which axis optionally may be the axis of both the outer tubular element and the inner elongate element, a rotation position may be obtained where an gas chamber is created. This may be obtained when the recipient is rotated to a position where the chord is brought substantially horizontal and the circle section is positioned above the chord. When the recipient is filled such that the level of the medium is lower than the chord, the space between medium level and chord may function as a gas chamber. A free medium surface is accommodated to exchange gas between the recipient, optionally being part of a bioreactor, and the exterior of the recipient, optionally the exterior of the bioreactor. The gas, which may be brought in or out the recipient using this chamber, will not be in direct contact with the medium.

The inner elongate wall may be a tubular wall.

The inner elongate wall may be coupled in a fixed position relative to the outer tubular wall.

The inner elongate element may be provided by an inner elongate element, the outer tubular element being provided by an outer tubular element, the inner elongate element and the outer tubular element being integrally moulded.

The inner elongate wall and the outer tubular wall may be rotatable one relative to the other.

The outer tubular wall may be a cylindrical tubular wall having a radial cross-section according to a plane perpendicular to its longitudinal direction, the radial cross-section having a shape selected from the group of a circle, oval, ellipse, square or rectangle.

The outer tubular wall and the inner elongate wall may be cylindrical tubular walls. The radial width of the inner space between the outer tubular wall and the inner elongate wall may be in a range between 5% and 45% of the diameter the outer tubular element.

The inner elongate wall may be positioned coaxially within the outer tubular wall.

The inner space may have a volume between 100 milliliters and 25 or even 100 liters.

The ratio between the diameter of the outer tubular wall and the length of the recipient may be between 10/25 and 100/25. Hence the recipient may have a diameter of the outer tubular element being 0.4 to 4 times the length of the recipient.

At least one of the first and second closures may comprise a coupling element for coupling the outer tubular wall to a driving unit for rotating the outer tubular wall.

The inner elongate wall may be provided by an inner hollow elongate element, the first closure sealing the first outer end of the inner elongate element.

The inner elongate wall may be provided by an inner hollow elongate element, the second closure sealing the second outer end of the inner elongate element.

The inner elongate wall may be a fluid permeable wall. According to some embodiments, the outer tubular wall may be a fluid permeable wall. According to some embodiments, the inner elongate wall and/or the outer tubular wall may be permeable for liquids and gas and are suitable for retaining the packing.

Fluid permeable walls may be provided using porous material comprising pores, hence providing porous walls. Alternatively, the fluid permeable walls may be provided using perforated material comprising apertures, hence providing perforated walls. The fluid permeable walls are however provided with pores or apertures small enough to prevent the packing to pass from one side of the wall to the other.

According to a second aspect, a bioreactor for cell cultivation is provided. The bioreactor comprises one or more recipients according to the first aspect of the disclosure. The one or more recipients may be positioned with their tubular axis substantially horizontally and rotatably along a longitudinal axis.

The longitudinal axis of the recipient is an axis parallel to the longitudinal direction of the outer tubular wall. The one or more recipients may be rotatably mounted in a reactor vessel. Optionally the outer tubular wall is provided with apertures or is made from a porous, e.g. liquid and gas permeable material. When a fluid permeable outer tubular wall is rotated in a vessel partially filled with medium, so that only part of the outer tubular wall is submerged in the medium, the packing may be provided with medium flowing into the annular volume through the outer tubular wall. Part of the medium may be dragged along with the packing when the recipient is to rotate in the vessel. The use of such fluid permeable material also simplifies the control of the method. Closed recipients require the use of connectors and conducts to assay or refresh medium and gas. This requires proper position of the connectors and adequate timing of the sampling or the refreshment. In the embodiments wherein one or more recipients with fluid permeable outer walls are rotatably placed within a larger vessel, the sampling of the gas and the medium can be performed permanently within this vessel.

The one or more recipients may comprise flexible conduits for coupling the inner space of the recipient to a storage of medium and/or gas.

The bioreactor may comprise a driving means capable of alternately rotating the outer tubular wall clockwise and counter clockwise.

Optionally the inner elongate wall is synchronically rotated with the outer tubular wall.

The bioreactor may further comprise a driving roller for rotating the outer tubular wall by contacting the outer surface of the outer tubular wall.

The recipient may comprise a magnetic element. The bioreactor may further comprise a magnetic element, which co-operates with the magnetic element of the recipient. Both magnetic elements may be positioned such that the rotation of the magnetic element of the bioreactor around the axis of rotation will induce the rotation of the magnetic element of the recipient, hence will rotate the outer tubular wall of the recipient and optionally the complete recipient.

According to another aspect, a method for cultivating cells is provided. The method comprises the steps of:
a) introducing into the recipient according to the first aspect of the present invention:
   anchorage-dependent cells or non anchorage-dependent cells, and
   cultivation medium,
b) positioning the recipient with the longitudinal direction of the outer tubular wall substantially horizontally, the outer tubular wall being rotatable along an axis parallel to its longitudinal direction and
c) rotating the outer tubular wall of said recipient along said axis.

Optionally the inner elongate wall may be synchronically rotated with the outer tubular wall.

According to some embodiments, the cultivation of cells may be obtained by adherent cell growth.

According to some embodiments, the cultivation of cells may be obtained by suspension culture.

According to some embodiments, the upper fluid level of the cultivation medium may reach to at least the inner elongate wall when the recipient is brought in at least one radial position.

The upper fluid level, in this case liquid level, is provided in the inner space so that, when brought in at least one radial position, the upper fluid level contacts at least the inner elongate wall at one point. The inner elongate wall may be partially submerged in the medium when brought in at least one radial position.

According to some embodiments, the upper fluid level of the cultivation medium may be below the inner elongate wall when the recipient is brought in at least one radial position.

The upper fluid level, in this case liquid level, is provided in the inner space so that, when brought in at least one radial position, the upper fluid level does not contact the inner elongate wall at one point. As such, a free liquid surface is provided, above which a gas chamber is present. This gas chamber may be used for exchanging gas from or to the exterior of the recipient.

According to some embodiments, the volume of medium provided in the open space may be between 25 and 100% of the annular volume of the inner space of the recipient.

According to some embodiments, the outer tubular wall may be rotated alternatively clockwise and counterclockwise.

According to some embodiments, the rotation about said axis may be performed with a maximum angular velocity of between 0.1 and 25 rotations per minute.

According to some embodiments, the tubular wall may have an outer surface being oriented opposite to the inner space. The outer surface may have a maximum linear velocity of up to 10 cm/second.

According to some embodiments, the method may comprise the step of assaying and/or replacing medium and/or and gas in the inner space of the recipient.

According to a further aspect of the disclosure, a recipient for cell cultivation having an inner compartment for cell growth, comprises:
an outer tubular wall extending in a longitudinal direction, the outer tubular wall delimiting an outer boundary of the inner compartment in a radial direction;
first and second ends delimiting the inner compartment at the first respectively the second outer end of the outer tubular wall; and
a packing in the inner compartment comprising a fiber matrix.

In one embodiment, the first and second ends comprise removable caps. The first end may include an inlet and the second end may include an outlet. One or more fluid-permeable partitions may be positioned within the compartment for contacting the fiber matrix.

A rotator may be provided for rotating at least the packing. The rotator may comprise a roller for contacting the outer tubular wall of the recipient. The rotator may comprise a magnetic coupling.

A closed loop may be provided for delivering fluid to and from the compartment. A reservoir may be connected to the closed loop, and at least one sensor associated with the reservoir. The sensor may be selected from the group consisting of a temperature sensor, a position sensor, an optical sensor, a pH-sensor, an oxygen sensor, a $CO_2$-sensor, an ammonia sensor, a cell density sensor, or combinations of any of the foregoing.

In any embodiment, the fibers of the fiber matrix may comprise non-woven PET fibers.

A further aspect of the disclosure pertains to an apparatus for growing cells, comprising:
a roller bottle including an outer tubular wall extending in a longitudinal direction, first and second ends delimiting the compartment at the first respectively the second outer end of the outer tubular wall, and a packing in the compartment comprising a fiber matrix; and
a rotator for rotating the packing.

In one embodiment, first and second spaced first fluid-permeable partitions positioned within the compartment. A closed loop may be provided for delivering fluid to and from the compartment. A reservoir may be connected to the closed loop, and at least one sensor associated with the reservoir.

A further aspect of the disclosure pertains to a recipient for cell cultivation having an inner compartment for cell growth, comprising an outer tubular wall extending in a longitudinal direction, the outer tubular wall delimiting an outer boundary of the inner compartment in the longitudinal direction; and first and second ends delimiting the compartment at the first respectively the second outer end of the outer tubular wall; a packing in the compartment; and at least one fluid-permeable partition positioned in the compartment. In one embodiment, the partition comprises a perforated plate.

Still a further aspect of the disclosure relates to a method for culturing cells, comprising:
providing a roller bottle with a packing;
delivering a fluid to the roller bottle; and
rotating the packing.

In one embodiment, the step of rotating the packing (which may comprise a fiber matrix) includes rotating the roller bottle after the delivering step. The step of rotating the packing may comprise rotating the packing while the roller bottle remains stationary. The step of withdrawing fluid from the roller bottle may occur during the rotating step. The method may further include the step of sensing a characteristic of the fluid after the withdrawing step, and further including the step of returning the withdrawn fluid to the roller bottle during the delivering step.

A further aspect of the disclosure pertains to a recipient for cell cultivation having an inner compartment for cell growth, comprising:

an outer tubular wall extending in a longitudinal direction, the outer tubular wall delimiting an outer boundary of the inner compartment in the longitudinal direction;

first and second ends delimiting the compartment at the first respectively the second outer end of the outer tubular wall;

a packing in the inner compartment; and a conduit for transmitting fluid for cultivating cells in the inner compartment.

In one embodiment, the conduit comprises a coiled tubing. The recipient may further comprise an inlet for connecting to the coiled tubing, and an outlet for connecting to the coiled tubing. The conduit may comprise a first coiled tubing connected to the inlet and a second coiled tubing connected to the outlet. The inlet and the outlet may be provided on a common wall of the recipient. The inlet may be connected to a tube extending within the inner compartment to deliver fluid at a location remote from the outlet. A sensor may be connected to the recipient, said sensor associated with a coiled transmission line. A gas injector, such as a rotameter, may be connected to the conduit. A rotary joint may be provided for connecting with the conduit.

In any embodiment, a system for cultivating cells may include the recipient positioned on a recirculation loop including the conduit. The conduit may be connected at one end to the recipient and at another end to a reservoir. The reservoir may include a filter and/or a sensor.

Yet a further aspect of the disclosure pertains to a method for culturing cells, comprising:

(a) rotating a container including a fixed packing in a first direction; and (b) after the rotating in the first direction, rotating the container in the second direction.

The method may include delivering a fluid to the container during the step of rotating in the first direction. The method may comprise delivering a fluid to the container during the step of rotating in the first direction. The method may further include the step of connecting the container to a conduit comprising a coiled tube prior to the delivering step. The fluid may comprise a liquid, and the method further includes the step of injecting a gas into the liquid prior to the delivering step.

In any embodiment, the rotating may be completed for at least one full rotation of the container in each of the first and second directions. The rotating may be completed for at least two full rotations of the container in each of the first and second directions. The rotating may be completed for at least three full rotations of the container in each of the first and second directions. The method may further include repeating steps (a) and (b).

Particular and preferred aspects are set out in the accompanying independent and dependent claims. Features from the dependent claims may be combined with features of the independent claims and with features of other dependent claims as appropriate and not merely as explicitly set out in the claims.

Although there has been constant improvement, change and evolution of devices in this field, the present concepts are believed to represent substantial new and novel improvements, including departures from prior practices, resulting in the provision of more efficient, stable and reliable devices of this nature.

The teachings permit the design of improved bioreactors for cultivation of cells, either using suspension culture or adherent cell growth. The recipients may be used for e.g. prokaryotic cells such as bacterial cells, and particularly eukaryotic cells such as yeast cells, plant cells, insect cells, mammalian and more particularly human cells or antibody producing hybridoma cells or stem cells. According to one embodiment, these cells themselves are harvested. In other embodiments, cell derived products are collected such as viruses obtained from infected cells, antibodies, recombinant nucleic acid constructs (e.g. plasmids), recombinant proteins or cellular metabolites such as vitamins or hormones.

The above and other characteristics, features and advantages will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

BRIEF DESCRIPTION OF THE DRAWINGS

FIG. 1 is a schematic side view of a recipient according to the first aspect of the disclosure, as well as a radial cross-section of this recipient, the radial cross-section in FIG. 1a being made according to a plane perpendicular to the central axis of the recipient.

FIG. 2 is a schematic view of a longitudinal cross-section of a recipient according to the first aspect of the disclosure, the section being made according to a longitudinal plane parallel to and comprising the central axis of the recipient.

FIG. 6 is a longitudinal cross-section of a bioreactor comprising a plurality of recipients according to the first aspect, the section of FIG. 6a being made according to a longitudinal plane parallel to and comprising the central axes of the recipients.

FIG. 7 schematically shows a cross-section and a longitudinal section of a recipient as shown in FIG. 3, mounted on a cooperating driving shaft.

FIGS. 10 and 10a-10c illustrate an alternate embodiment.

FIGS. 11-19 depict further aspects of the disclosure.

Figure 3:
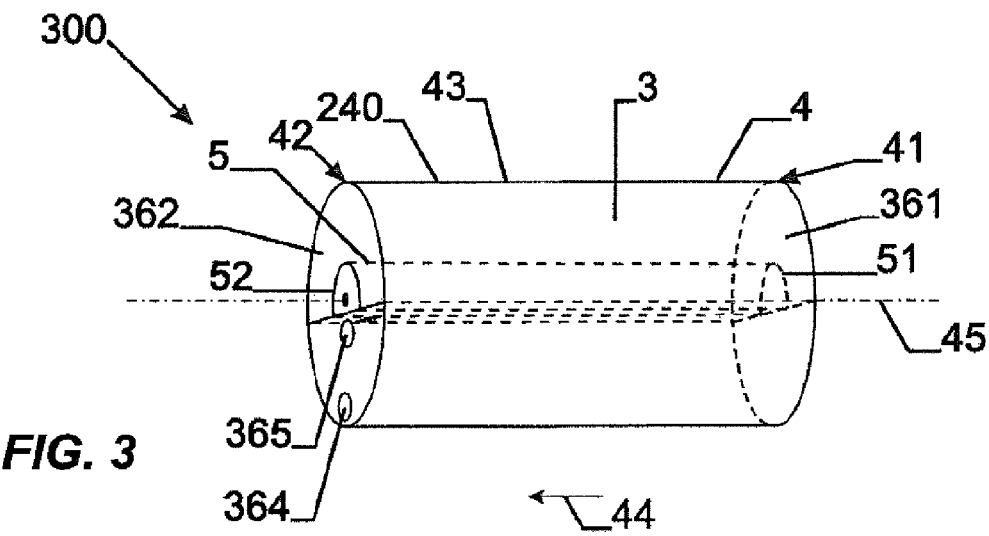
FIG. 3 is a side view and a radial cross-section of a recipient according to the first aspect, the cross-section of FIG. 3a being made according to a plane perpendicular to the central axis of the recipient.
Figure 3A:
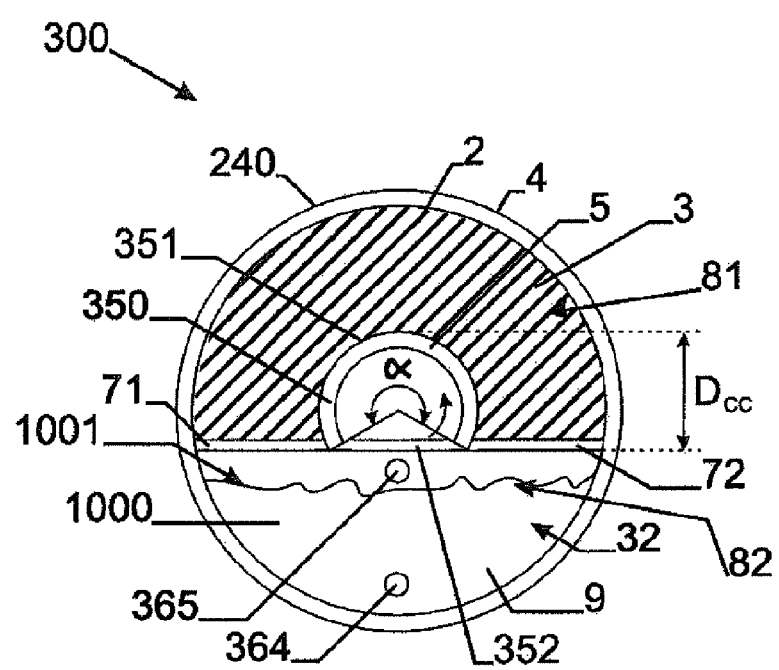

In the different figures, the same reference signs refer to the same or analogous elements.

DESCRIPTION OF ILLUSTRATIVE EMBODIMENTS

The disclosure includes descriptions of particular embodiments and with reference to certain drawings, but the invention is not limited thereto but only by the claims. The drawings described are only schematic and are non-limiting.

In the drawings, the size of some of the elements may be exaggerated and not drawn on scale for illustrative purposes. The dimensions and the relative dimensions do not correspond to actual reductions to practice of the invention.

Furthermore, the terms first, second, third and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present disclosure, the only relevant components of the device are A and B.

Similarly, it is to be noticed that the term "coupled", also used in the claims, should not be interpreted as being restricted to direct connections only. The terms "coupled" and "connected", along with their derivatives, may be used. It should be understood that these terms are not intended as synonyms for each other. Thus, the scope of the expression "a device A coupled to a device B" should not be limited to devices or systems wherein an output of device A is directly connected to an input of device B. It means that there exists a path between an output of A and an input of B which may be a path including other devices or means. "Coupled" may mean that two or more elements are either in direct physical or electrical contact, or that two or more elements are not in direct contact with each other but yet still co-operate or interact with each other.

Reference throughout this specification to "one embodiment" or "an embodiment" means that a particular feature, structure or characteristic described in connection with the embodiment is included in at least one embodiment. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claims require more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

Additionally, an element described herein of an apparatus embodiment is an example of a means for carrying out the function performed by the element for the purpose of carrying out the invention.

In the description provided herein, numerous specific details are set forth. However, it is understood that embodiments of the invention may be practised without these specific details. In other instances, well-known methods, structures and techniques have not been shown in detail in order not to obscure an understanding of this description.

The following terms are provided solely to aid in the understanding of the invention.

"Radial direction" is to be understood as perpendicular to the axis of the smallest circumscribing cylinder.

"Circumscribing" is to be understood as to be provided, e.g. to construct or be constructed, around a geometrical figure so as to touch as many points as possible.

The term "tubular" is to be understood as a hollow volume, being elongated in a longitudinal direction.

The term "cylindrical" is to be understood as having the form of a cylinder. A cylinder is to be understood as an object having a volume bounded by a surface traced by a straight line moving parallel to a fixed straight line (i.e. the longitudinal direction) and intersecting a fixed or closed curve and two parallel planes cutting this surface.

A circular segment, or "truncated circle", is one of the two parts obtained when a circle is intersected with a line, thereby providing two intersecting points. Of each part, the path from the first to the second intersecting point along the line is called the chord. For each part, there is a path from the first to the second intersecting point along the circle, being the circle section. For each part, the angle over which the first intersecting point is to be rotated along the circle section to bring the first intersecting point to coincide with the second intersecting point is called the central angle of the circular segment. The height of the circular segment is the distance between chord and circle section at half the central angle. The height may be more than the radius of the circle of which the shape is a segment. The surface of the circular segment may be more than half the surface of the circle of which the shape represents a segment.

The inventive concepts disclosed herein will now be described by a detailed description of several embodiments. It is clear that other embodiments of the invention can be configured according to the knowledge of persons skilled in the art without departing from the true spirit or technical teaching of the invention, the invention being limited only by the terms of the appended claims.

A first embodiment of a recipient 1 according to the first aspect of the disclosure, which recipient 1 is suitable to be used in a bioreactor, is shown in FIG. 1. The recipient 1 for cell cultivation has an inner space 2, which may be annular as shown but may take other forms as noted herein. The space 2 contains packing 3. When the recipient is to be used for cell culture the packing 3 should be compatible with cell growth.

In the annular configuration shown, the inner space 2 has an annular volume delimited by:

an outer tubular wall 4 having a first outer end 41 and a second outer end 42 and a longitudinal wall 43 extending in longitudinal direction, referred to by arrow 44. The outer tubular wall 4 delimits an outer boundary of the annular volume in longitudinal direction 44;

a first and a second closure (61, 62) delimiting and closing the annular volume at the first outer end 41 respectively the second outer end 42 of the outer tubular wall 4;

an inner elongate wall 5 having a first outer end 51 oriented towards the first outer end of the outer tubular wall, and a second outer end 52 oriented towards the second outer end of the outer tubular wall 4. The inner elongate wall 5 is positioned within the outer tubular wall 4. The inner elongate wall 5 extends in longitudinal direction 44 and delimits an inner boundary of the annular volume, the inner boundary being encompassed by the outer boundary.

The second outer end 52 of the inner elongate wall 5 coincides with the second closure 62. As an example, the outer tubular wall is provided by a cylindrical outer tubular element 40. The inner elongate wall 5 may be provided by a solid inner cylindrical element 50, such as a cylindrical rod. The outer tubular element 40 is a cylindrical tubular element, and has a central axis 45, parallel to the longitudinal direction. The inner cylindrical element 50 and the outer tubular element 40 may be coaxially mounted.

The first outer end of the inner cylindrical element 50 may comprise a coupling element 53 to couple the inner cylindrical element 50, and by means of the closures 61 and 62 being fixed to the inner cylindrical element 50 and the outer tubular element 40, the outer tubular element 40 as well, to a drive mechanism, e.g. a motor of the bioreactor. The second closure 62 is provided with a connector, suitable to couple the recipient to a medium or gas source, for providing and/or extracting medium and/or gas to and/or from the inner space 2. This connector, or alternatively additional connectors may be provided to the first closure 61 or the second closure 62.

The inner space 2 is at least partially filled with packing 3. As an example the packing may be mineral carriers such as silicates, calcium phosphate, organic compounds such as porous carbon, natural products such as chitosan, polymers or biopolymers compatible with cells growth. The packing can have the form of beads with regular or irregular structure, or may comprise woven or non-woven microfibers of a polymer or any other material compatible with cell growth. The packing can also be provided as a single piece with pores and or channels.

Optionally, the packing may have a porosity P in the range of 50% to 98%. The term porosity P is the volume of air present in a given volume of the material, and expressed as percentage of the given volume of the material. The porosity can be measured by measuring the weight Wx per volume of the porous material, and using the formula:

$$P=100-(1-Wx/Wspec)$$

wherein Wspec is the specific weight of the material. The porous material may be one solid unit of porous material, or may be a plurality of individual units, such as grains, chips, beads, fibres or fiber agglomerates.

Upon moving the recipient, the packing, in particular the porous material, may rest in a fixed relative position to the recipient, or may move within and relative to the recipient or, as the case may be, within the compartment of the recipient.

The recipient is to be rotated about its axis 45, optionally at a rotational speed of between 0.1 and 25 rotations per minute.

As best visible in the radial cross-section of FIG. 1a, the inner space is partially filled with cultivation medium, such as cell cultivation medium 15. As an example, the liquid level 18 at least contacts the inner elongate wall 5, or, as shown in the embodiment of FIG. 1, the inner elongate wall 5 is partially submerged in the medium 15. The part of the packing 3 positioned under the liquid level 18 is wetted by the cultivation medium, such as cell cultivation medium. The packing 3 positioned above the liquid level 18 is in contact with the gas or air present in the inner space 2. When the recipient is rotated in one direction about the axis 45, e.g. clockwise rotated as indicated by arrow 17, the cultivation medium, such as cell cultivation medium 15 rotates in opposite, say anti-clockwise direction (indicated by 19) relative to the packing 3. The cultivation medium, such as cell cultivation medium 15, is passed through the complete packing 3 according to a plug flow. Upon rotation, e.g. clockwise, of the recipient, the cultivation medium, such as cell cultivation medium forces the gas or air 16 at the leading edge 20 of the plug flow to displace anti-clockwise. At the tailing edge 21 of the medium 15, an optionally limited depression is created, causing gas or air 16 to be sucked towards the trailing edge. As such the medium 15 and the gas or air 16 passes through the complete packing 3.

As an alternative shown in FIG. 2, the inner elongate wall 5 of an alternative recipient 200 may be provided by a cylindrical tubular element 250. The same references refer to similar features as disclosed in relation to recipient 1 of FIG. 1.

The outer tubular wall 4 is provided by an outer tubular element 240. The inner elongate wall 5 is provided by an elongate cylindrical tubular element 250. The outer tubular element 240 and the elongate cylindrical tubular element 250 are fixed to two removable closures 261 and 262. The first closure 261 is provided with a coupling element 253 for coupling the recipient to a driving means for rotating the recipient along an axis in longitudinal direction 44. The first closure 261 further comprises a connector 263 for connecting the inner space 2 to a conduit, such as a flexible tube.

As an example, the outer tubular element may be a glass tube, having a length L of e.g. 110 mm and an inner diameter Do of, for example, 135 mm. The inner elongate element may be a polyvinylidenefluoride (PVDF) tube having an outer diameter Di of, for example, 88.9 mm. The outer ends of the inner elongate element, hence of the inner elongate wall, coincide with the closures 261 and 262. The closures may be stainless steel or PVDF annular discs, which may be attached to the inner and outer element using silicone. The first closure 261, which may be provided with a connector 263, has a coupling element 253, having an outer diameter Dce of, for example, about 35 mm.

The inner space 2 is at least partially filled with packing 3. As an example, the packing may be identical or similar to the packing in the embodiment of FIG. 1.

Another alternative recipient 300 is shown in FIG. 3. The same references refer to similar features as disclosed in relation to recipient 1 of FIG. 1.

The recipient further comprises 2 fluid permeable dividers 71 and 72, dividing the inner space in 2 compartments 81 and 82. The fluid permeable dividers 71 and 72 extend from the inner elongate wall 5 to the outer tubular wall 4 and from the first closure 361 to the second closure 362 in the longitudinal direction 44 parallel to the direction of the tubular axis 45. One compartment 81 is provided with the packing 3. One compartment 82 is not provided with the packing. The fluid permeable dividers may be provided with pores, such as by using porous material for providing porous dividers, or are provided with apertures, in any case allowing passage of liquid, i.e. cultivation medium, and gas. The dividers 71 and 72 are however provided with pores or apertures small enough to prevent the packing to pass from one side of the divider to the other.

The outer tubular wall 4 is provided by an outer tubular element 240 having a racial cross-section along a plane perpendicular to the longitudinal direction, which cross-section has the shape of a circle.

The inner elongate wall 5 is provided by an inner elongate element 350 having a racial cross-section along a plane perpendicular to the longitudinal direction, which cross-section has the shape of a truncated circle or circular segment. In one embodiment the circle segment has a circle section 351 and a chord 352. For example the height of the circle segment has the dimensions of 200 mm (Dcc), 400 mm (Do), 240 mm (Di) and 125 mm (L). The dividers 71 and 72 are in this embodiment coplanar with the chord 352 of the circle segment.

The second closure 362 of the two closures 361 and 362, is provided with two connectors 364 and 365. The first connector 364 is provided near the outer tubular wall 4. The second connector 365 is provided near the inner elongate wall 5. As is shown in FIG. 3, when the recipient is only partially filled with cultivation medium 1000, which medium has a liquid surface 1001, the recipient may be rotated to such a position that the liquid does not contact the inner elongate wall 5, but remains on a given distance from the inner elongate wall 5. When the recipient is brought in this position, the first connector may be used to remove or provide medium to the compartment 82, which is not filled with packing 3. Gas may be removed or provided above the medium liquid surface by means of connector 365. By rotation of the recipient either clockwise or counter clockwise, e.g. over an angle of up to 360° or even more, the medium will pass through to one of the two dividers, more particular through the divider which will gradually be submerged in the medium. The medium will slowly flow through the packing, as the packing gradually will pass through the medium because of the rotation. Due to the rotation of the recipient, the medium will pass and flow through the complete packing according to a plug flow. A uniform contact between medium and packing throughout the annular volume will occur. Once a part of the packing has passed through the medium, the medium will gradually seep out of the packing and hence the gas in the recipient may again contact the packing, allowing the cells to grow uniformly throughout the packing.

Figure 4A:
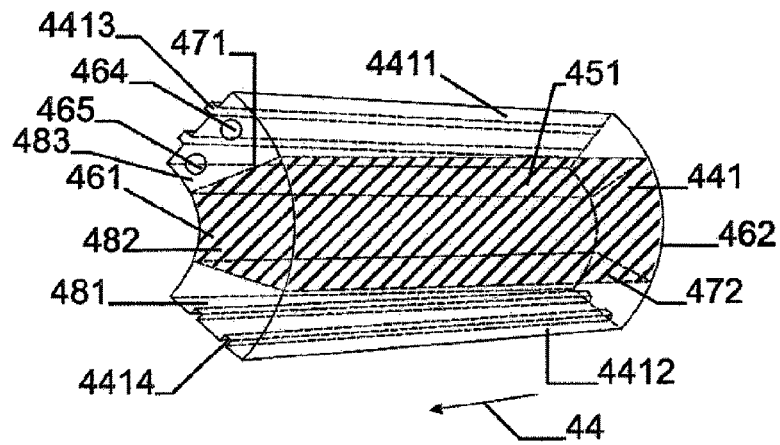
FIG. 4a-4c are radial cross-sections of alternative recipients according to the first aspect, the cross-sections being made according to a plane perpendicular to the central axis of the recipient, and a side view of an annular section being part of the recipient.
Figure 4B:
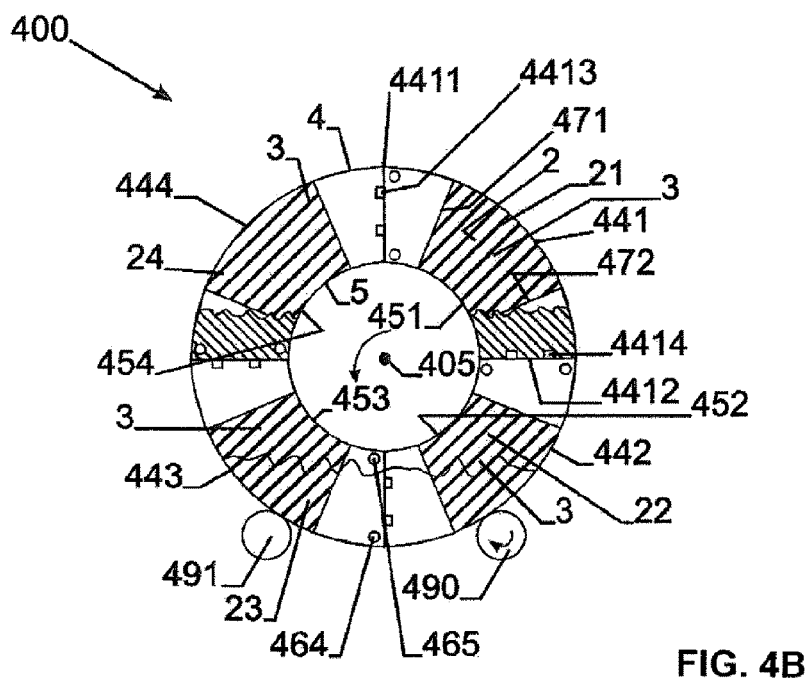

Turning to FIGS. 4a and 4b, still another alternative recipient 400 is shown. The annular volume of the inner space 2 is provided by a plurality of annular sections 21, 22, 23 and 24, in this particular case four annular quarters. Each of the sections 21, 22, 23 and 24 provides one part of the outer tubular wall 4 by means of an outer tubular wall section 441, 442, 443 respectively 444. Each of the sections provides one part of the inner elongate wall 5 by means of an inner elongate wall section 451, 452, 453 respectively 454.

Each of the sections has two radially extending section walls. As an example section 21 has two radially extending section walls 4411 and 4412. These section walls are liquid and gas impermeable. Each of the section walls is provided with mounting means 4413 and 4414 allowing adjacent sections to couple one to the other.

A first and a second section closure 461 and 462 delimiting and closing the volume of the annular sections at the first respectively the second outer end of the outer tubular wall. The section closures together form the first respectively second closure of the annular volume 2 of the recipient.

As can be understood with further reference to FIGS. 4a-4b, each of the sections may further be provided with two fluid permeable dividers 471 and 472, dividing the inner space of each annular section in three compartments 481, 482 and 483. The fluid permeable dividers 471 and 472, e.g. porous dividers extend from the inner elongate wall 5 to the outer tubular wall 4 and from the first closure 461 to the second closure 462 in the longitudinal direction 44 parallel to the direction of the tubular axis 405. One compartment 482 is provided with the packing 3. Two compartments 481 and 483 are not provided with the packing. The dividers may be similar or identical as the dividers of the recipient of FIG. 3.

Similar as shown in FIG. 3, for each annular section 21, 22, 23 and 24, a first connector 464 is provided near the outer tubular wall 4. The second connector 465 is provided near the inner elongate wall 5. As is clear from FIG. 4, each of the sections may function as an independent recipient section of the recipient 400, when the recipient is rotated about the axis 405. The packing in each of the sections is provided with medium, which is present in this section depending upon the radial position of the section.

By mounting the sections, in this embodiment four sections 21, 22, 23 and 24, a recipient with an outer tubular wall and an inner elongate wall is obtained, of which the annular volume is closed at the two outer ends of the outer tubular wall by means of two closures. Because the coupling of the sections is provided by mounting and coupling two radially extending section walls, the combination of two contiguous section walls form a liquid and gas impermeable divider extending from the inner elongate wall 5 to the outer tubular wall 4 and from the first closure to the second closure in the longitudinal direction 44 parallel to the direction of the tubular axis 405. This embodiment has the advantage that each of the sections may be provided with different medium for a different cell culture. Also, in case of an incorrect functioning of the packing of reaction in one of the sections, only one section is to be replaced.

As is shown in this embodiment, the rotation of the recipient (or any other recipient disclosed herein) may be provided by a rotator. In one example, this rotator may include contacting the outer surface of the outer tubular wall with at least two supporting wheels 490 and 491 of which at least one is driven.

Figure 4C:
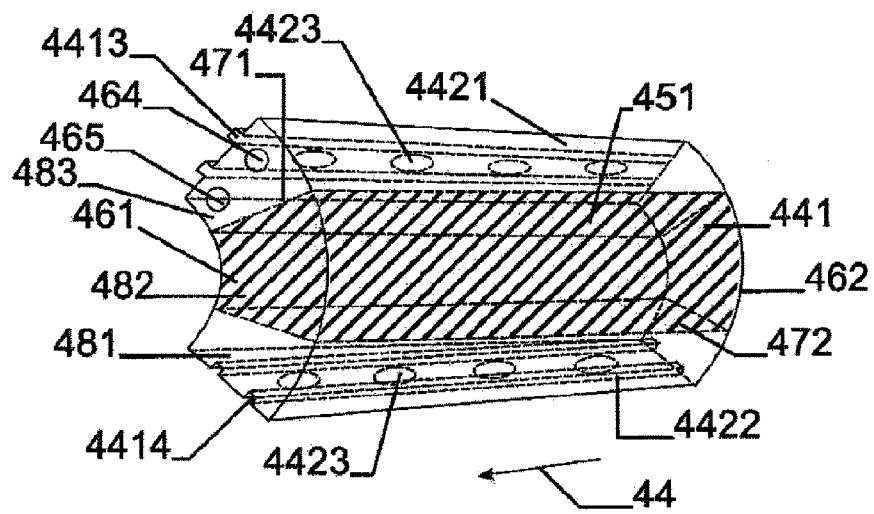
Figure 4D:
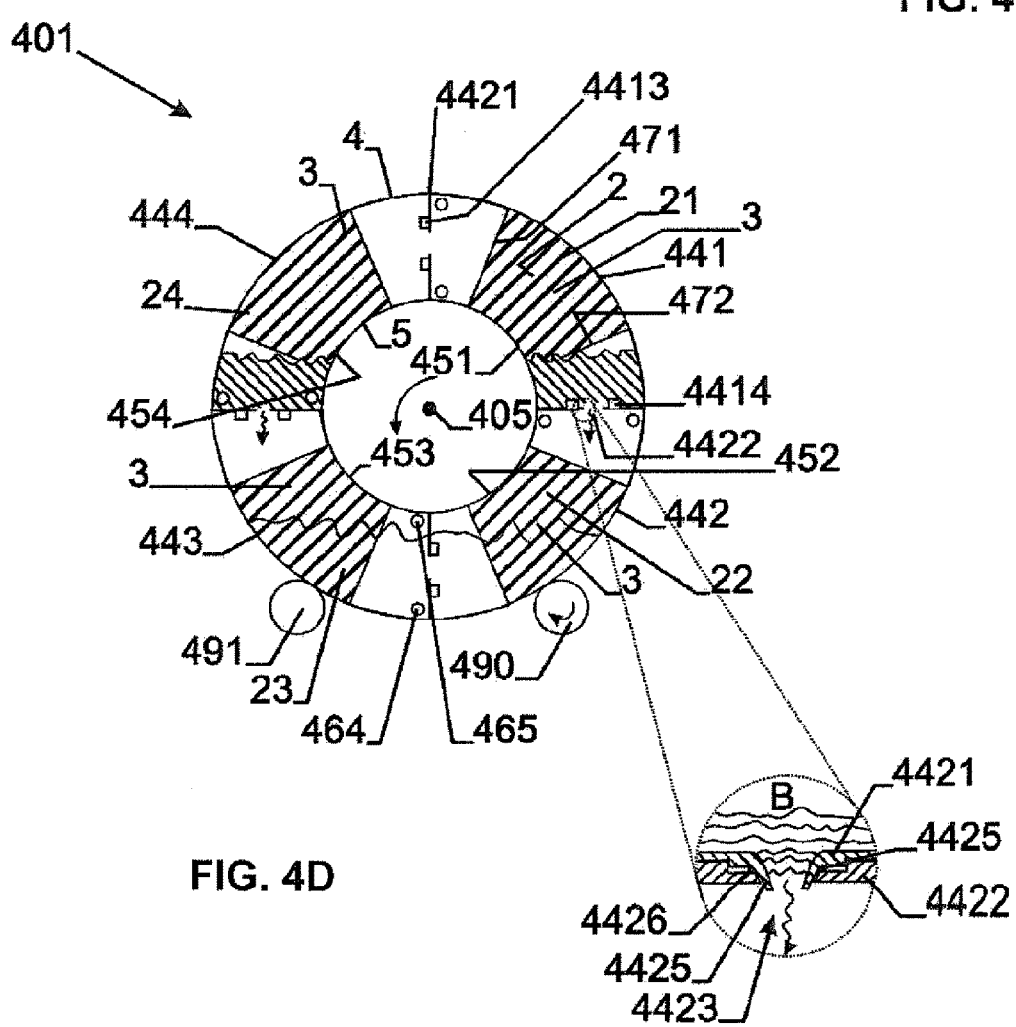

FIGS. 4c and 4d show an alternative embodiment of a recipient 401. In FIG. 4c, identical references refer to identical parts and elements as in FIG. 4a. In this embodiment, each of the sections of the recipient 401 has two radially extending section walls 4421 and 4422. These section walls 4421 and 4422 are liquid and gas permeable. Each section wall 4421 comprises a number of apertures 4423, each of these apertures finding a corresponding aperture in a second section wall 4422 of an adjacent compartment. As shown in the detail B, the aperture of the first section wall 4421 may be provided with an outwardly extending rim 4425 which extends through the corresponding aperture of the second section wall 4422. Optionally a seal 4426 is provided around the apertures in the adjacent section walls to prevent medium from leaking between the contacting walls. In alternative embodiments, a flexible tubing is placed between the recipients instead of seals.

Figure 5A:
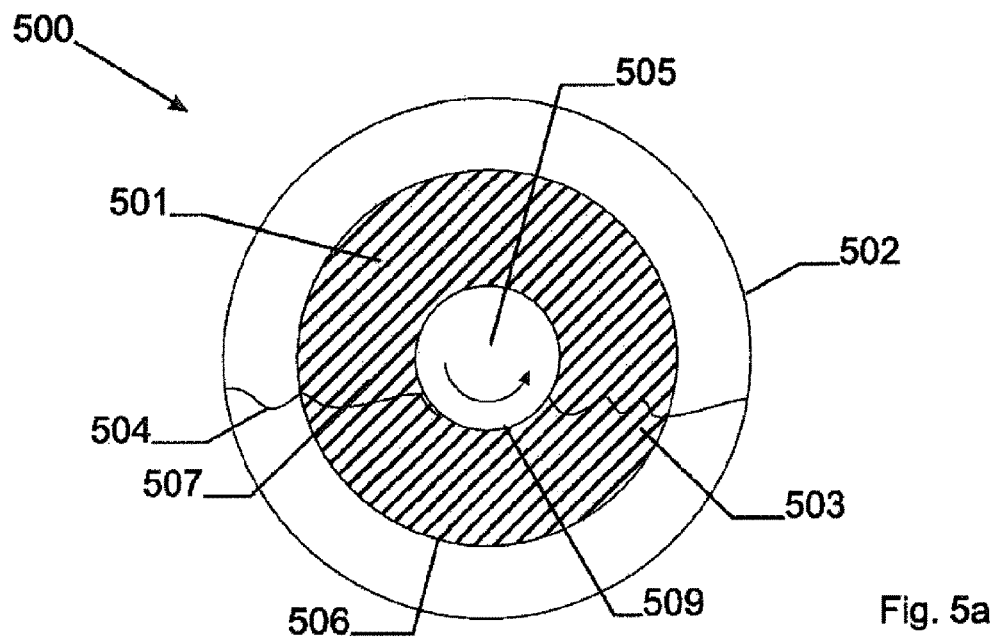
FIG. 5a and FIG. 5b are radial cross sections of a bioreactor comprising a recipient according to the first aspect, the cross-sections being made according to a plane perpendicular to the central axis of the recipient.
Figure 5B:
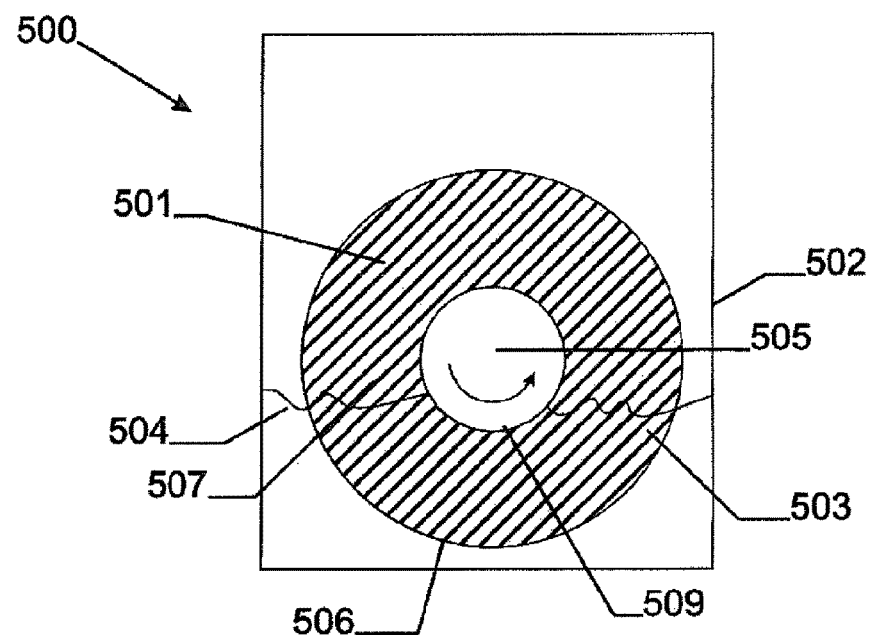

An embodiment of a bioreactor 500 is shown in FIG. 5*a* and FIG. 5*b*. At least one recipient 501, similar to the recipient 1 disclosed in FIG. 1, is rotatably mounted in a vessel 502, which may have any suitable radial cross-section such as e.g. circular as shown in FIG. 5*a*, or polygonal such as rectangular (optionally square) as shown in FIG. 5*b*. The vessel is partially filled with cultivation medium 503, so the liquid level 504 optionally does not raise higher than the axis 505 of the bioreactor, but at least contacts the inner elongate wall 509. The recipient 501 is rotated about this axis 505, which is identical to the longitudinal axis of the recipient 501. The longitudinal axis of the recipient 501 is an axis parallel to the longitudinal direction of the outer tubular wall 506. Optionally the outer tubular wall 506 is provided with apertures or is made from a porous, e.g. liquid and gas permeable material. When such fluid permeable outer tubular wall 506 is rotated in a vessel 502 partially filled with medium 503, so that only part of the outer tubular wall 506 is submerged in the medium, the packing 507 may be provided with medium flowing into the annular volume 508 through the outer tubular wall 506. Part of the medium may be dragged along with the packing when the recipient is to rotate in the vessel. The skilled person understands that other features as set out in relation to the recipients 1, 200, 300 or 400 may be added to the recipient 501.

Another bioreactor 600 is shown in FIGS. 6 and 6A. At least one recipient 601, but in this figure two recipients 601 and 611, which are similar to the one disclosed in FIG. 1, are rotatably mounted in a vessel 602. The vessel is partially filled with cultivation medium 603, so the liquid level 604 optionally does not raise higher than the axis 605 of the bioreactor, but at least contacts the inner elongate wall 609. The recipient 601 is rotated about this axis 605, which is identical to the longitudinal axis of the recipient 601. The longitudinal axis of the recipient is an axis parallel to the longitudinal direction of the outer tubular wall. Optionally the outer tubular wall 606 is provided with apertures or is made from a porous, e.g. liquid and gas permeable material. When such fluid permeable outer tubular wall 606 is rotated in a vessel 602 partially filled with cultivation medium 603, so that only part of the outer tubular wall 606 is submerged in the cultivation medium 603, the packing 607 may be provided with cultivation medium 603 flowing into the annular volume 608 through the outer tubular wall 606. Part of the cultivation medium 603 may be dragged along with the packing when the recipient is to rotate in the vessel.

At least one of the recipients, in this embodiment recipient 601, comprises a magnetic element 612. The bioreactor further comprises a magnetic element 613, which co-operates with the magnetic element 612 of the recipient. Both magnetic elements 613 and 612 are positioned such that the rotation of the magnetic element 613 of the bioreactor 600 around the axis 605 of rotation will induce the rotation of the magnetic element 612 of the recipient 601, hence will rotate the complete recipient 601. The adjacent recipients may be mounted on a common shaft 620, around which they rotate. The adjacent recipients 601 and 611 may be coupled to each other in a fixed position, so the rotation of recipient 601 induces the rotation of the recipient 611 as well.

The skilled person understands that recipients having a liquid and gas impermeable outer tubular wall, but which have connectors for connecting the recipient to a gas or medium storage by optionally a flexible tubing, may be mount and rotated in a similar way as set out with regard to FIG. 5 and FIG. 6. The skilled person understands that other features as set out in relation to the recipients 1, 200, 300 or 400 may be added to the recipient 601.

As shown in FIG. 7, the recipients, such as recipient 300 of FIG. 3, may be rotated by means of a driving system for providing a bioreactor. The recipient is mounted on a rotatable shaft 701, which is rotatable about an axis of rotation coinciding with the axis 45 of the recipient 300. The shaft 701 is profiled and fits in a unique rotational position within the inner void 702 of the inner elongate element 350. As such, by controlling the rotational position of the shaft 701, the position of the recipient about axis 45 is unambiguously defined. The driving system may further comprise a motor 703, such as a linear motor, or any other suitable means to precisely control the rotation of the shaft 701. A clamp 704 screw or any suitable means to prevent the recipient to displace in longitudinal direction over the shaft 701 may fix the position of the recipient 300 on the shaft 701 in longitudinal direction 705.

It is understood that optionally more than one recipient 300 may be mounted on a common shaft 701.

Figure 8A:
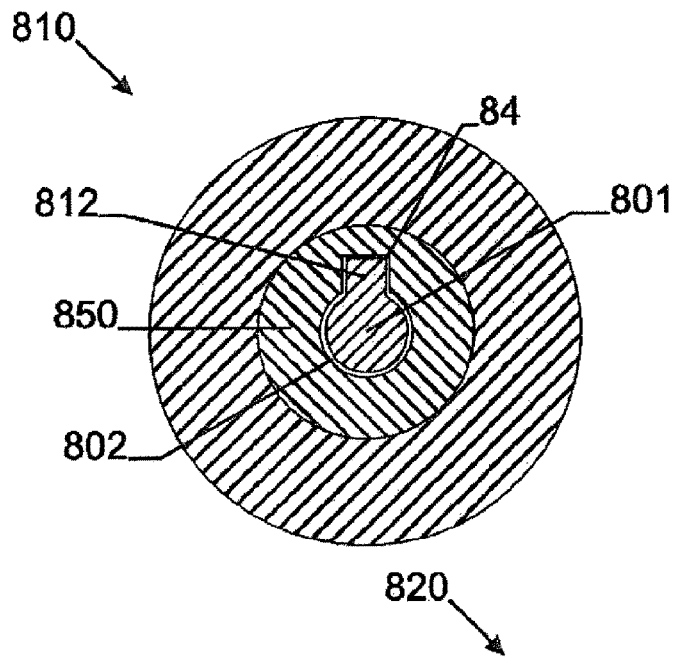
FIGS. 8a-8c schematically shows alternative recipients according to embodiments, mounted on a cooperating driving shaft.
Figure 8B:
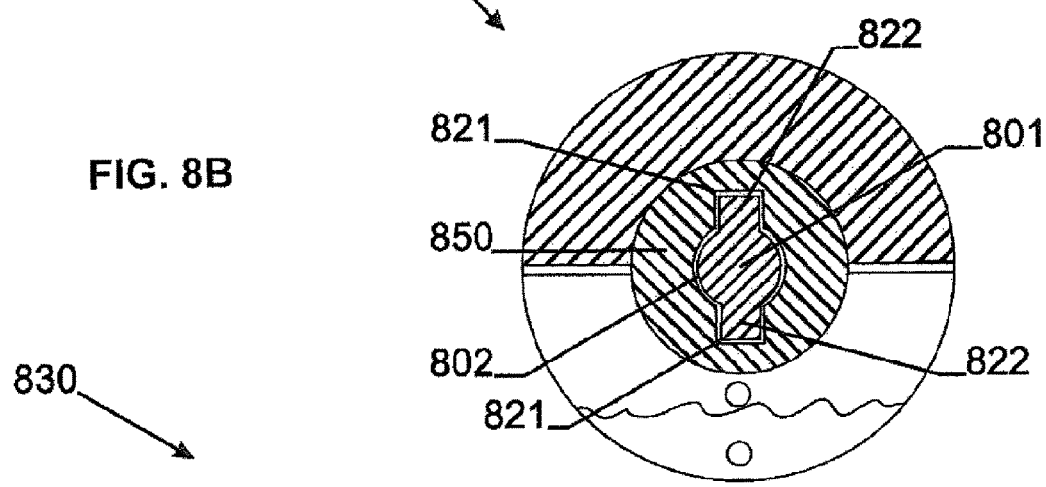
Figure 8C:
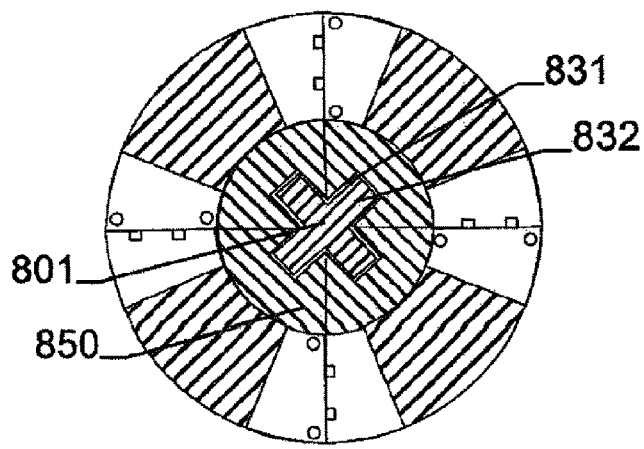

FIGS. 8*a*-8*c* show a cross-section of alternative examples of recipients mounted on a cooperating driving shaft 801. The shape of the inner void 802 of the inner elongate element 850 and the perimeter of the shaft 801 are chosen such that the shaft and the recipient may be mounted in a limited or even in a unique way.

In the recipient 810, which is similar as the recipient of FIG. 1, the inner elongate element has a longitudinal recess 811 in the inner wall of the inner elongate element. A ridge 812 on the shaft 801 fits into this recess 811. The recipient fits in an unambiguous way on the shaft. The ridge 812 may be slidingly moveable in the recess 811.

In recipient 820 is a recipient similar as the recipients of FIG. 1. The inner elongate element has two longitudinal recesses 821 in the inner wall of the inner elongate element. Two mutually perpendicular ridges 822 on the shaft 801 fit into these recesses 821. The recipient 820 fits in two ways on the shaft, the first position being 180° rotated about the axis relative to the second position. The ridges 822 may be slidingly moveable in the recesses 821.

Recipient 830 is a recipient similar as the recipients of FIGS. 4*a* and 4*c*. The inner elongate element has four longitudinal recesses 831, one in each of the inner walls of the inner elongate element provided by a compartment. The shaft has a substantially cross-like cross-section, comprising four mutually perpendicular ridges 832 on the shaft 801. Each of the ridges fits into a recess 831 of one of the compartments. The recipient 830 fits in four ways on the shaft. The ridges 832 may be slidingly moveable in the recesses 831.

The skilled person understands that other features of the recipients as described relative to the FIGS. 1 to 6, may be combined with a driving system as disclosed by means of FIGS. 7 and 8.

Figure 9:
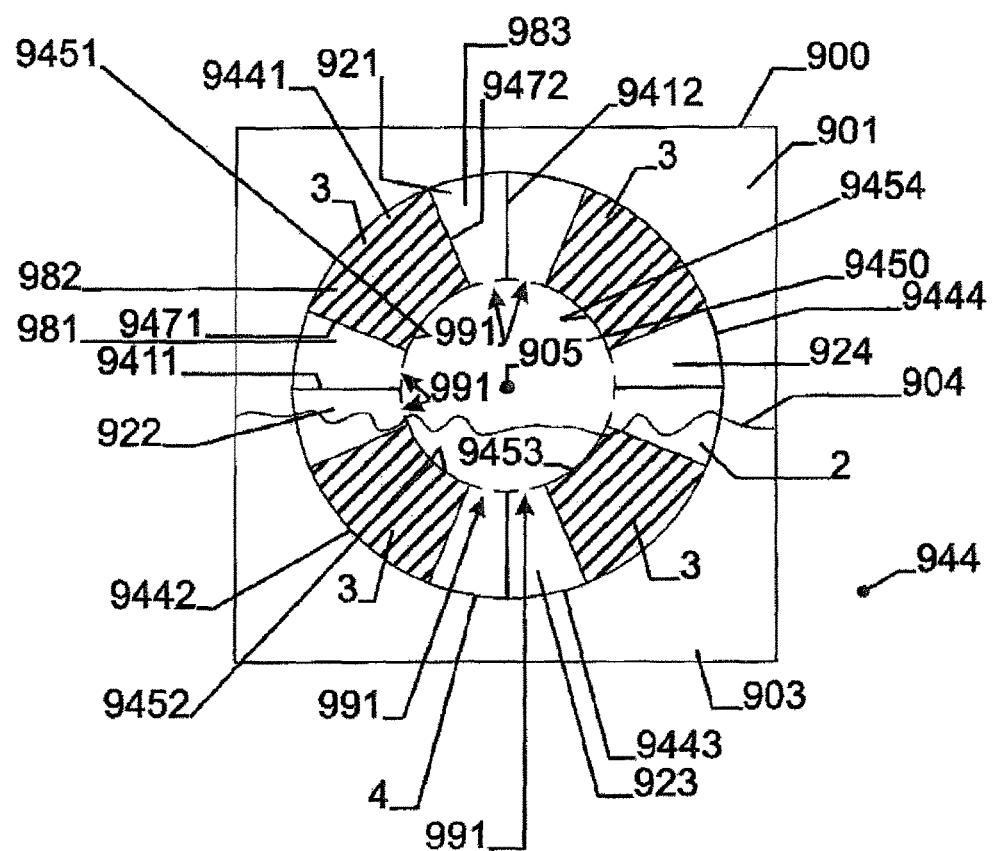
FIG. 9 schematically shows a radial cross-section of a bioreactor comprising a recipient being an embodiment according to the disclosure.

Turning to FIG. 9, still another alternative recipient 901 according to the present disclosure is shown as being part of a bioreactor 900. The same references refer to similar features as disclosed in relation to recipient 1 of FIG. 1.

The volume of the inner space 2 is provided by a plurality of segments 921, 922, 923 and 924, in this particular case four quarters.

Each of the sections provides one part of the outer tubular wall 4 by means of an outer tubular wall part 9441,9442, 9443 respectively 9444. Each of the segments provides one part of the inner elongate wall 5 by means of an inner elongate wall part 9451, 9452, 9453 respectively 9454.

Each of the segments has two radially extending segment walls. As an example segment 921 has two radially extending segment walls 9411 and 9412. These segment walls are liquid and gas impermeable.

A first and a second closure delimits and closes the volume 2 of the segments at the first respectively the second outer end of the outer tubular wall, hence closing the volume 2 of the recipient.

Each of the segments may further be provided with two fluid permeable dividers 9471 and 9472, dividing the inner space of each segment in 3 compartments 981, 982 and 983. The fluid permeable dividers 971 and 972 extend from the inner elongate wall 5 to the outer tubular wall 4 and from the first closure to the second closure in the longitudinal direction 944 parallel to the direction of the tubular axis 905. One compartment 982 is provided with the packing 3. Two compartments 981 and 983 are not provided with the packing. The dividers may be similar or identical to the dividers of the recipient of FIG. 3.

The recipient 901 is rotatably mounted in a vessel 900. The vessel is partially filled with cultivation medium 903, so the liquid level 904 optionally does not rise higher than the axis 905 of the bioreactor 900. The recipient 901 is rotated about this axis 905, which is identical to the longitudinal axis of the recipient 901. The longitudinal axis of the recipient is an axis parallel to the longitudinal direction of the outer tubular wall.

Each of the compartments 981 and 983 are provided with appropriate apertures, such as longitudinal slits 991 along the inner wall 9451, 9452, 9453 respectively 9454. Each of the outer tubular wall parts 9441, 9442, 9443 respectively 9444 is provided with apertures or is made from a porous, e.g. liquid and gas permeable material. When such fluid permeable outer tubular wall is rotated in a vessel 900 partially filled with cultivation medium 903, so that only part of the outer tubular wall is submerged in the cultivation medium 903, the packing 3 in the compartments may be provided with cultivation medium 903 flowing into the volume through the outer tubular wall. Part of the cultivation medium 903 may be dragged along with the packing when the recipient is to rotate in the vessel. The cultivation medium 903 further may fill the inner void 9450 of the inner elongate wall. Through the apertures 991, the cultivation medium 903 may flow in or out of the sections 981 and 982, optionally to the adjacent section 982 respectively 981.

FIGS. 10 and 10a-10c illustrate a further example of a recipient 1000 that includes a body 1002 forming a longitudinal wall and ends in the form of caps 1004, 1006. The caps 1004, 1006 may be removable as shown, and in the connected position form a fluid-tight seal for containing any fluid within the body 1002. Each cap 1004, 1006 may include an opening 1004a, 1006a forming an inlet or outlet for receiving the culture medium (see FIG. 11), but the inlet and outlet could each be provided in the same cap as well, or in the longitudinal wall of the body 1002.

At least one, and in the illustrated case, a pair of fluid-permeable structures, such as perforated partitions 1008, 1010 are provided forming a compartment 1012 for containing any packing (see FIG. 12). The perforations in each partition 1008 or 1010 may be provided in a shape and size to control the flow and residence time of the fluid in the compartment 1012, and may be the same or different among the partitions.

The packing may comprise any of the structures described above, but may in one embodiment comprise fibers (such as woven or non-woven polyester fibers) and, in particular, non-woven PET fibers. The packing may be provided in a manner such that it completely occupies the compartment of the recipient 1000, and thus circumferentially contacts the inner surfaces of the wall of the body 1002, as well as the fluid-permeable structures (e.g., partitions 1008, 1010).

FIG. 11 illustrates that the recipient 1000 may be associated with a rotary device 1100. The device 1100 may include a pair of rollers 1102 for receiving, supporting, and rotating the recipient 1000 about the longitudinal axis of the body. The recipient 1000 in this case may be provided with a generally cylindrical body 1002 adapted for engaging and being rotated by the rollers 1102 to help distribute any fluid (e.g., the culture medium, or any rinsing or recovery agent) through any packing present in the compartment.

Tubular connectors 1014, 1016 may also be provided in association with the inlet 1004a and outlet 1006a for delivering fluid to the compartment. This may be done while the recipient 1000 is stationary or while it is rotating. In the latter case, the connectors 1014, 1016 may be connected in a manner that permits relative rotation, such as by using a rotary joint created by way of a snap-fit engagement or using a bearing. Seals, such as O-rings, may be used to help prevent any leakage and help maintain the sterile conditions desirable for cell culturing.

One advantage of the recipient 1000 of FIGS. 10-12 is the simplicity of the arrangement. For example, in the illustrated embodiment, the recipient 1000 includes no sensors, probes, mixers, or the like. In the event it is desirable to include such structures, this is possible, and may be accomplished by connecting the recipient 1000 in a closed loop with a reservoir 1200, as shown in FIG. 13. The reservoir 1200 may include any number of sensors or the like for measuring one or more characteristics of the circulated fluid, and may include a single use vessel (such as a flexible bag) to avoid the need for cleaning and sterilization. A pump, such as a peristaltic pump 1202, may also be provided for circulating the fluid through the loop.

A further aspect of this disclosure is now described with reference to FIGS. 14-16. In this embodiment, the recipient 1300 may be constructed according to any of the above details (thus forming a roller bottle), and includes an inlet 1302 and an outlet 1304. Each of the inlet and outlet 1302, 1304 may be connected to a conduit that permits rotation of the recipient 1300 without unduly biding or twisting the conduit in a manner that does not interfere with the fluid transmission, and thus may allow for the continuous flow of fluid to and from the recipient 1300 while it is rotated. Specifically, the conduit may comprise a coiled tube 1306 having an open end for connecting to the inlet 1302 or outlet 1304, respectively, and may at the opposite ends associate with any fluid reservoir. A suitable pumping arrangement may also be provided for moving fluid through the conduit and the recipient 1300.

FIGS. 15 and 16 illustrate one possible manner of use of the embodiment of the recipient of FIG. 14, including the conduit adapted for permitting rotation. Specifically, as shown in FIG. 15, the recipient 1300 may be rotated in a first direction, such as clockwise, for one or more complete rotations, using a suitable rotator (such as rollers 1308). The number of rotations possible without binding of the conduit may vary, but it is envisioned that 2-3 rotations should be possible at a minimum. The recipient 1300 may then be rotated in a second, opposite direction for one or more complete rotations. More specifically, the rotation may be for the number of rotations in the first direction to return the coiled tube to its home position, plus a corresponding number of rotations in the second direction for so long as the coiled tube does not bind or otherwise interfere with the fluid transmission. The rotation and counter-rotation may occur continuously or intermittently, and the same is true for the delivery and recovery of fluid via the conduit.

Turning back to FIG. 14, it can also be understood that, in the event the recipient 1300 includes a sensor 1310, it may also be connected to any source of energy used for sensing. In such case, any transmission line, such as a cable 1312, may also be coiled or spiral to accommodate the relative rotation in the manner contemplated above without twisting or binding. Again, it is desirable to place any sensors or the like in any recirculation loop, though, since this drives down the cost of the recipient 1300.

Figure 17:
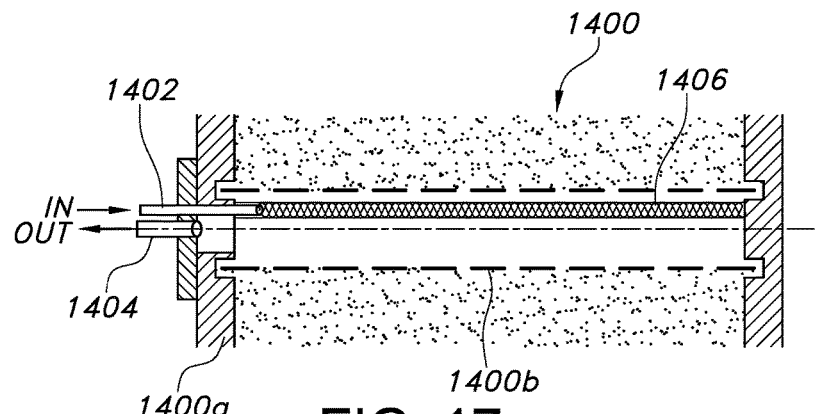

FIGS. 16 and 17 illustrate other details of proposed arrangements for a recipient 1400 in the form of a roller bottle. For instance, the inlet 1402 and outlet 1404 may be provided in a common wall 1400a. The inlet 1402 may also be associated with a tube positioned within a fluid permeable internal cylinder 1400b within the fixed bed, which helps to ensure the fluid introduced (gas, liquid, or both) does not simply immediately exit through the inlet 1402.

Figure 18:
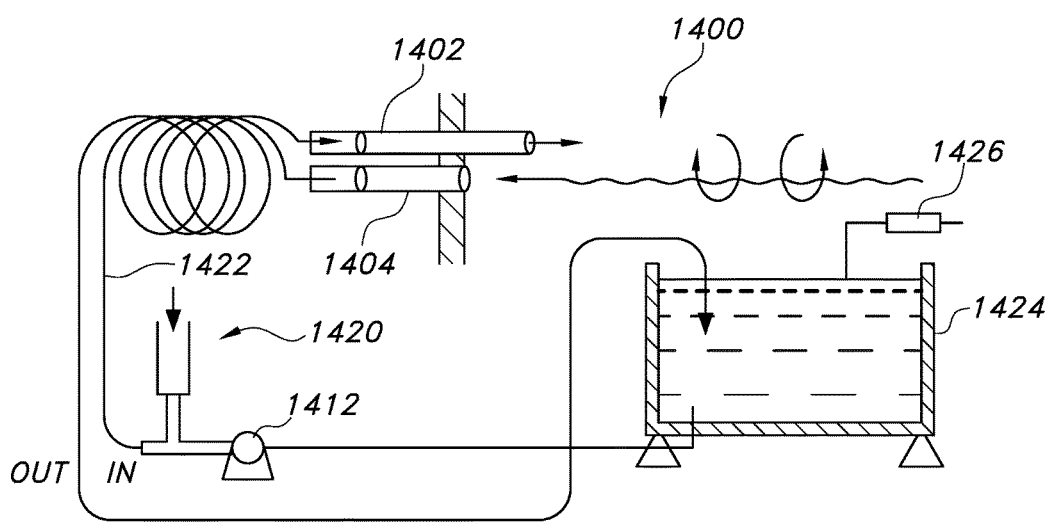
Figure 19:
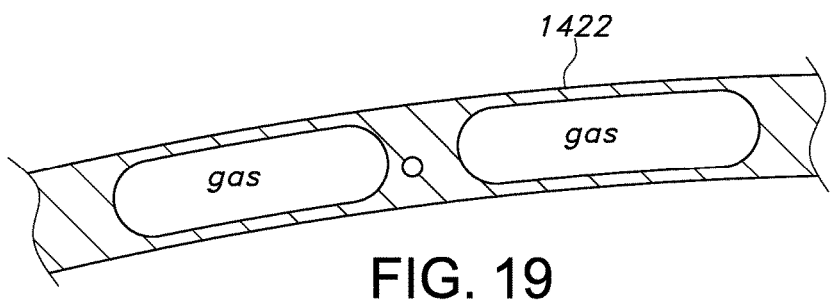

FIG. 17 also shows that a gas may be introduced into a liquid by placing an injector 1420, such as a rotameter, in the recirculation loop. The placement may be immediately upstream of the inlet 1402. As indicated in FIG. 18, this manner of gas introduction in connection with liquid flow advantageously helps to reduce the incidence of foaming and improve the mass transfer rate, since the gas remains in pockets separated by the liquid (see FIG. 19). FIG. 18 also shows that the transmission line 1422 associated with the outlet 1404 returns to the reservoir 1424, which may be vented through a filter 1426 as shown, to avoid a vent for direct connection with the recipient 1400.

It is to be understood that other elements may be added to the recipients and the bioreactors. As an example the inner elongate wall may be an elongate tubular, optionally cylindrical wall. The inner void of the inner tubular wall may be used to accommodate one or more sensors, such as temperature sensors, position sensors (e.g. for defining the orientation of the recipient relative to the axis of rotation), optical sensors (e.g. for generating data on the colour of the cultivation medium, such as cell cultivation medium), pH-sensors, oxygen sensors (such as Dissolved Oxygen (DO)-sensors), $CO_2$-sensors, ammonia sensors or cell biomass sensors (e.g. turbidity densitometers). Such sensors may additionally or optionally be located in or on the closures.

The recipient may also accommodate perfusion, continuous addition of fresh nutrient medium and the withdrawal of an equal volume of used medium, allowing the realisation of cell cultivation conditions that are approximated as closely as possible to the in vivo situation. The combination of a perfusion cell culture with e.g. an enzyme glucose biosensor allows the glucose consumption of the cell culture to be monitored continuously.

It is also understood that heating elements, such as heating blankets, may be provided to the outer and optionally the inner wall for heating or maintaining the temperature of the medium and the packing in the recipient.

EXAMPLES

Example 1: Oxygen Transport to Packing Materials

A cylindrical recipient in PVC with an outer wall, a perforated inner wall, two closures with one containing a cap, (length 120 mm, internal diameter 75 mm and external diameter 90 mm), was filled with 66 g of carriers composed of non-woven PET fibers (ca. 500 ml of packed-bed). The recipient was filled with 350 ml of water. The cap of recipient was closed by a silicon cap with sponge (Siliconsen culture plug, Fisher Scientific Bioblock). Oxygenation absorption kinetics were measured by a fluorometric DO probe (Presens, Regensburg, Germany) placed into the recipient (measurements were done when the probe was in liquid). The cap of recipient was opened and nitrogen gas was flushed into recipient until complete desorption of oxygen (0% DO). The recipient was closed with Silicosen culture plug and the bottle was placed on a roller station. The sponge of the plug allowed the inflow of air. The kinetics of oxygen absorption was followed by measuring the increase of oxygen concentration vs. time. The experiment was performed at different rotation speeds. At 2.60 rpm, 5 rpm and 6.65 rpm, the DO in the liquid has increase from 0% to 75% in respectively ca. 6 min, 5 min and 4 min, (corresponding to a $K_l \cdot a$ of 13 $h^{-1}$, 16 $h^{-1}$, 38 $h^{-1}$).

Example 2: Small Scale Cell Growth in Partially Filled Recipients

A cylindrical recipient with a glass outer wall, a perforated stainless steel inner wall, one glass closure and one stainless steel closure containing a cap, (length 120 mm, internal diameter 70 mm and external diameter 130 mm), having a inner space volume of 1350 nil and delimited by 4 dividers (defining an angle of 90 degrees) contained a section of 10 ml of packed-bed filled with 1.33 g of carrier composed of non-woven PET fibers. The cap of the recipient was closed by a Siliconsen culture plug. The recipient was sterilized and filled with 250 ml of culture medium (MEM with 1.8 g/L of glucose, 5% of fetal bovine serum and 1% of non-essential amino-acid) and inoculated with $12.2 \times 10^6$ MDBK cells (Madin-Darby Bovine Kidney Cells) (i.e. $1.2 \times 10^6$ cells/$cm^3$ of packed-bed). The recipient was placed on rollers (6.5 rpm), in an incubator at 37° C. The gas supply through the cap was sufficient to grown cells for a period of 7 days. After 5 days of cultivation, the cell density reached $18.2 \times 10^6$ cells/$cm^3$ and the medium was exchanged. After 7 days, the cell density reached $46.0 \times 10^6$ cells/$cm^3$ (i.e. a biomass increase of 38.4 times in 7 days).

Other arrangements for accomplishing the objectives of the recipients embodying the invention will be obvious for those skilled in the art. It is to be understood that although preferred embodiments, specific constructions and configurations, as well as materials, have been discussed herein for various embodiments of devices, various changes or modifications in form and detail may be made without departing from the scope of this invention as defined by the appended claims. For example, any formulas given above are merely representative of procedures that may be used. Functionality may be added or deleted from the block diagrams and operations may be interchanged among functional blocks. Steps may be added or deleted to methods described within the scope of the invention.

The invention claimed is:

1. A system for cell cultivation, comprising a recipient having an inner compartment for cell growth, the recipient comprising:
   an outer tubular wall extending in a longitudinal direction, the outer tubular wall delimiting an outer boundary of the inner compartment in a radial direction;
   first and second ends delimiting the inner compartment at the first outer end and the second outer end of the outer tubular wall;
   a packing in the inner compartment comprising a fiber matrix; and one or more fluid-permeable partitions positioned within the inner compartment for contacting the fiber matrix;

the system having a rotator for rotating at least the packing.

2. The system of claim 1, further wherein the first and second ends of the recipient comprise removable caps.

3. The system of claim 1, wherein the first end of the recipient includes an inlet to the inner compartment and the second end of the recipient includes an outlet to the inner compartment.

4. The system of claim 1, wherein the rotator comprises a roller for contacting the outer tubular wall of the recipient.

5. The system of claim 1, wherein the rotator comprises a magnetic coupling.

6. The system of claim 1, further including a closed loop for delivering fluid to and from the compartment.

7. The system of claim 6, further including a reservoir connected to the closed loop.

8. The system of claim 7, further including at least one sensor associated with the reservoir.

9. The system of claim 8, wherein the sensor is selected from the group consisting of a temperature sensor, a position sensor, an optical sensor, a pH-sensor, an oxygen sensor, a $CO_2$-sensor, an ammonia sensor, a cell density sensor, or combinations of any of the foregoing.

10. The system of claim 1, wherein the fiber matrix comprises woven or non-woven polyester fibers.

11. An apparatus for growing cells, comprising:

a roller bottle including an outer tubular wall extending in a longitudinal direction, first and second ends delimiting a compartment at a first outer end and the second outer end of the outer tubular wall, and a packing in the compartment comprising a fiber matrix;

a rotator for rotating the packing; and one or more fluid-permeable partitions positioned within the compartment for contacting the fiber matrix.

12. The apparatus of claim 11, further including first and second spaced fluid-permeable partitions positioned within the compartment in a spaced apart relationship.

13. The apparatus of claim 11, further including a reservoir connected to the closed loop.

14. The apparatus of claim 13, further including at least one sensor associated with the reservoir.

15. The apparatus of claim 11, further including a closed loop for delivering fluid to and from the compartment.

* * * * *